(12) United States Patent
Rodriguez-Navarro et al.

(10) Patent No.: US 11,357,525 B2
(45) Date of Patent: Jun. 14, 2022

(54) GRASPER WITH MAGNETICALLY-CONTROLLED POSITIONING

(71) Applicant: Levita Magnetics International Corp., San Mateo, CA (US)

(72) Inventors: Alberto Rodriguez-Navarro, San Francisco, CA (US); Ruth Beeby, Mountain View, CA (US); Steve Brunell, Fremont, CA (US); Mariel Fabro, San Francisco, CA (US)

(73) Assignee: LEVITA MAGNETICS INTERNATIONAL CORP., San Mateo, CA (US)

( * ) Notice: Subject to any disclaimer, the term of this patent is extended or adjusted under 35 U.S.C. 154(b) by 270 days.

(21) Appl. No.: 16/149,576

(22) Filed: Oct. 2, 2018

(65) Prior Publication Data

US 2019/0133631 A1    May 9, 2019

Related U.S. Application Data

(63) Continuation of application No. 15/098,262, filed on Apr. 13, 2016, now Pat. No. 10,130,381, which is a
(Continued)

(51) Int. Cl.
*A61B 17/29* (2006.01)
*A61B 17/02* (2006.01)
(Continued)

(52) U.S. Cl.
CPC .......... *A61B 17/29* (2013.01); *A61B 17/0218* (2013.01); *A61B 17/2812* (2013.01);
(Continued)

(58) Field of Classification Search
CPC ..... A61B 17/10; A61B 17/29; A61B 17/0218; A61B 17/2812; A61B 17/1285;
(Continued)

(56) References Cited

U.S. PATENT DOCUMENTS 2,678,228 A   5/1954 Gerhardt
2,863,444 A   12/1958 Winsten
(Continued)

FOREIGN PATENT DOCUMENTS

CA    2 748 471 A1   7/2010
CA    2733465 A1    9/2011
(Continued)

OTHER PUBLICATIONS

Extended European Search Report dated Aug. 22, 2019, for EP Application No. 17 736 483.3, filed on Jan. 6, 2017, 8 pages.
(Continued)

*Primary Examiner* — Vi X Nguyen
(74) *Attorney, Agent, or Firm* — Cooley LLP

(57) ABSTRACT

Described here are devices, systems, and methods for providing remote traction to tissue. Generally, the systems may include a grasper and a delivery device configured to releasably couple to the grasper. The grasper may have a first jaw and a second jaw and a main body having a barrel portion. The barrel portion may have a lumen extending therethrough, and a portion of the delivery device may be advanced through the lumen to rotate one or both of the jaws. The delivery devices may include a handle, a shaft, and a distal engagement portion. The delivery devices may further include an actuation rod which may be advanced through a barrel portion of a grasper to actuate the grasper. In some instances, the delivery device may further include a locking sheath, wherein the locking sheath is configured to temporarily couple to a grasper.

25 Claims, 13 Drawing Sheets

Related U.S. Application Data continuation of application No. 14/019,404, filed on Sep. 5, 2013, now Pat. No. 9,339,285.

(60) Provisional application No. 61/778,264, filed on Mar. 12, 2013.

(51) Int. Cl.
*A61B 17/28* (2006.01)
*A61B 17/00* (2006.01)
*A61B 17/10* (2006.01)

(52) U.S. Cl.
CPC .......... *A61B 17/2833* (2013.01); *A61B 17/10* (2013.01); *A61B 2017/00283* (2013.01); *A61B 2017/00473* (2013.01); *A61B 2017/00477* (2013.01); *A61B 2017/00876* (2013.01); *A61B 2017/2913* (2013.01); *A61B 2017/2925* (2013.01); *A61B 2017/2927* (2013.01); *A61B 2017/2931* (2013.01); *A61B 2017/2933* (2013.01); *A61B 2017/2934* (2013.01); *A61B 2017/2946* (2013.01)

(58) Field of Classification Search
CPC .............. A61B 17/2909; A61B 17/122; A61B 17/1227; A61B 2017/292
See application file for complete search history.

(56) References Cited

U.S. PATENT DOCUMENTS

| | | | |
|---|---|---|---|
| 3,146,381 A | 8/1964 | Louis | |
| 3,674,014 A | 7/1972 | Tillander | |
| 3,789,285 A | 1/1974 | Nishizawa | |
| 3,794,091 A | 2/1974 | Ersek et al. | |
| 4,364,377 A | 12/1982 | Smith | |
| 4,380,999 A | 4/1983 | Healy | |
| 4,706,668 A | 11/1987 | Backer | |
| 4,756,312 A | 7/1988 | Epley | |
| 4,901,405 A | 2/1990 | Grover et al. | |
| 4,915,435 A | 4/1990 | Levine | |
| 4,968,136 A | 11/1990 | Lim et al. | |
| 4,971,067 A | 11/1990 | Bolduc et al. | |
| 4,976,723 A | 12/1990 | Schad | |
| 4,997,436 A | 3/1991 | Oberlander | |
| 5,002,557 A | 3/1991 | Hasson | |
| 5,154,189 A | 10/1992 | Oberlander | |
| 5,156,608 A | 10/1992 | Troidl et al. | |
| 5,156,609 A | 10/1992 | Nakao et al. | |
| 5,282,806 A | 2/1994 | Haber et al. | |
| 5,300,081 A | 4/1994 | Young et al. | |
| 5,304,183 A | 4/1994 | Gourlay et al. | |
| 5,304,185 A | 4/1994 | Taylor | |
| 5,307,805 A | 5/1994 | Byrne | |
| 5,340,360 A | 8/1994 | Stefanchik | |
| 5,397,325 A | 3/1995 | Della Badia | |
| 5,411,535 A | 5/1995 | Fujii et al. | |
| 5,415,160 A | 5/1995 | Ortiz et al. | |
| 5,417,701 A | 5/1995 | Holmes | |
| 5,449,361 A | 9/1995 | Preissman | |
| 5,449,365 A | 9/1995 | Green et al. | |
| 5,450,842 A | 9/1995 | Tovey et al. | |
| 5,458,603 A | 10/1995 | Futch, Sr. | |
| 5,458,693 A | 10/1995 | Codorniu | |
| 5,465,711 A | 11/1995 | Moll et al. | |
| 5,496,317 A | 3/1996 | Goble et al. | |
| 5,499,986 A | 3/1996 | Dimarco | |
| 5,529,568 A | 6/1996 | Rayman | |
| 5,538,098 A | 7/1996 | Sparhawk | |
| 5,593,379 A | 1/1997 | Rayman | |
| 5,595,562 A | 1/1997 | Grier | |
| 5,654,864 A | 8/1997 | Ritter et al. | |
| 5,665,100 A | 9/1997 | Yoon | |
| 5,681,260 A | 10/1997 | Ueda et al. | |
| 5,728,121 A | 3/1998 | Bimbo et al. | |
| 5,733,292 A | 3/1998 | Gustilo et al. | |
| 5,749,881 A | 5/1998 | Sackier et al. | |
| 5,766,189 A | 6/1998 | Matsuno | |
| 5,782,748 A | 7/1998 | Palmer et al. | |
| 5,797,911 A | 8/1998 | Sherman et al. | |
| 5,797,939 A | 8/1998 | Yoon | |
| 5,848,969 A | 12/1998 | Panescu et al. | |
| 5,849,015 A | 12/1998 | Haywood et al. | |
| 5,888,196 A | 3/1999 | Bonutti | |
| 5,893,873 A | 4/1999 | Rader et al. | |
| 5,933,926 A | 8/1999 | Reiter | |
| 6,015,414 A | 1/2000 | Werp et al. | |
| 6,017,358 A * | 1/2000 | Yoon ..................... | A61B 17/29 600/564 |
| 6,096,038 A | 8/2000 | Michelson | |
| 6,099,537 A | 8/2000 | Sugai et al. | |
| 6,099,550 A | 8/2000 | Yoon | |
| 6,123,657 A | 9/2000 | Ishikawa et al. | |
| 6,126,647 A | 10/2000 | Posey et al. | |
| 6,127,757 A | 10/2000 | Swinbanks | |
| 6,165,180 A | 12/2000 | Cigaina et al. | |
| 6,173,715 B1 | 1/2001 | Sinanan et al. | |
| 6,212,419 B1 | 4/2001 | Blume et al. | |
| 6,216,028 B1 | 4/2001 | Haynor et al. | |
| 6,241,671 B1 | 6/2001 | Ritter et al. | |
| 6,311,082 B1 | 10/2001 | Creighton, IV et al. | |
| 6,315,709 B1 | 11/2001 | Garibaldi et al. | |
| 6,330,467 B1 | 12/2001 | Creighton, IV et al. | |
| 6,340,365 B2 | 1/2002 | Dittrich et al. | |
| 6,358,196 B1 | 3/2002 | Rayman | |
| 6,371,973 B1 | 4/2002 | Tepper | |
| 6,398,791 B1 | 6/2002 | Que et al. | |
| 6,399,146 B1 | 6/2002 | Harris et al. | |
| 6,401,723 B1 | 6/2002 | Garibaldi et al. | |
| 6,440,133 B1 | 8/2002 | Beale et al. | |
| 6,458,146 B1 | 10/2002 | Kramer | |
| 6,459,924 B1 | 10/2002 | Creighton, IV et al. | |
| 6,464,710 B1 | 10/2002 | Foster | |
| 6,488,615 B1 | 12/2002 | Mitchiner et al. | |
| 6,523,919 B1 | 2/2003 | Israelsen et al. | |
| 6,537,196 B1 | 3/2003 | Creighton, IV et al. | |
| 6,551,304 B1 | 4/2003 | Whalen et al. | |
| 6,594,517 B1 | 7/2003 | Nevo | |
| 6,630,879 B1 | 10/2003 | Creighton, IV et al. | |
| 6,632,229 B1 | 10/2003 | Yamanouchi | |
| 6,641,595 B1 | 11/2003 | Moran et al. | |
| 6,656,199 B1 | 12/2003 | Lafontaine | |
| 6,677,752 B1 | 1/2004 | Creighton, IV et al. | |
| 6,689,119 B1 | 2/2004 | Di Caprio et al. | |
| 6,702,804 B1 | 3/2004 | Ritter et al. | |
| 6,705,989 B2 | 3/2004 | Cuschieri et al. | |
| 6,719,765 B2 | 4/2004 | Bonutti | |
| 6,761,681 B2 | 7/2004 | Schmid et al. | |
| 6,786,219 B2 | 9/2004 | Garibaldi et al. | |
| 6,817,364 B2 | 11/2004 | Garibaldi et al. | |
| 6,824,511 B1 | 11/2004 | Bell et al. | |
| 6,916,314 B2 | 7/2005 | Schneider et al. | |
| 7,017,584 B2 | 3/2006 | Garibaldi et al. | |
| 7,094,245 B2 | 8/2006 | Adams et al. | |
| 7,169,104 B2 | 1/2007 | Ueda et al. | |
| 7,182,089 B2 | 2/2007 | Ries | |
| 7,182,775 B2 | 2/2007 | De Guillebon et al. | |
| 7,189,198 B2 | 3/2007 | Harburn et al. | |
| 7,264,584 B2 | 9/2007 | Ritter et al. | |
| 7,300,400 B2 | 11/2007 | Brown | |
| 7,311,107 B2 | 12/2007 | Harel et al. | |
| 7,313,429 B2 | 12/2007 | Creighton, IV et al. | |
| 7,314,063 B2 | 1/2008 | Egli | |
| 7,341,063 B2 | 3/2008 | Garbibaldi et al. | |
| 7,344,553 B2 | 3/2008 | Opolski et al. | |
| 7,390,298 B2 | 6/2008 | Chu | |
| 7,416,335 B2 | 8/2008 | Munger | |
| 7,429,259 B2 | 9/2008 | Cadeddu et al. | |
| 7,431,726 B2 | 10/2008 | Spence et al. | |
| 7,566,038 B2 | 7/2009 | Scott et al. | |
| 7,618,435 B2 | 11/2009 | Opolski | |
| 7,686,827 B2 | 3/2010 | Hushka | |
| 7,691,103 B2 | 4/2010 | Fernandez et al. | |

(56) References Cited

U.S. PATENT DOCUMENTS

| | | |
|---|---|---|
| 7,691,731 B2 | 4/2010 | Bet et al. |
| 7,708,756 B2 | 5/2010 | Nobis et al. |
| 7,736,356 B2 | 6/2010 | Cooper et al. |
| 7,766,810 B2 | 8/2010 | Ohdaira |
| 7,769,427 B2 | 8/2010 | Shachar |
| 7,772,950 B2 | 8/2010 | Tunay |
| 7,774,046 B2 | 8/2010 | Werp et al. |
| 7,780,054 B2 | 8/2010 | Wales |
| 7,799,050 B2 | 9/2010 | Hensley et al. |
| 7,837,612 B2 | 11/2010 | Gill et al. |
| 7,850,591 B2 | 12/2010 | Spector |
| 7,942,885 B2 | 5/2011 | Sixto, Jr. et al. |
| 7,963,903 B2 | 6/2011 | Ghiron et al. |
| 7,966,059 B2 | 6/2011 | Creighton, IV et al. |
| 7,967,830 B2 | 6/2011 | Ayala et al. |
| 8,038,612 B2 | 10/2011 | Paz |
| 8,043,290 B2 | 10/2011 | Harrison et al. |
| 8,057,472 B2 | 11/2011 | Walker et al. |
| 8,060,184 B2 | 11/2011 | Hastings et al. |
| 8,066,715 B2 | 11/2011 | Ducharme |
| 8,074,657 B2 | 12/2011 | Scott et al. |
| 8,082,035 B2 | 12/2011 | Glukhovsky |
| 8,133,254 B2 | 3/2012 | Dumbauld et al. |
| 8,136,888 B2 | 3/2012 | Suzuki et al. |
| 8,137,268 B2 | 3/2012 | Van Lue |
| 8,157,149 B2 | 4/2012 | Olson et al. |
| 8,187,286 B2 | 5/2012 | Jugenheimer et al. |
| 8,197,494 B2 | 6/2012 | Jaggi et al. |
| 8,226,690 B2 | 7/2012 | Altarac et al. |
| 8,235,272 B2 | 8/2012 | Nicholas et al. |
| 8,241,322 B2 | 8/2012 | Whitman et al. |
| 8,246,529 B2 | 8/2012 | Riehl et al. |
| 8,252,021 B2 | 8/2012 | Boulnois et al. |
| 8,267,854 B2 | 9/2012 | Asada et al. |
| 8,301,226 B2 | 10/2012 | Csavoy et al. |
| 8,303,495 B2 | 11/2012 | Ducharme |
| 8,313,497 B2 | 11/2012 | Walberg et al. |
| 8,316,861 B2 | 11/2012 | Brewer et al. |
| 8,316,862 B2 | 11/2012 | Shapiro et al. |
| 8,333,695 B2 | 12/2012 | Cuschieri |
| 8,343,171 B2 | 1/2013 | Farritor et al. |
| 8,360,972 B2 | 1/2013 | Paz |
| 8,364,277 B2 | 1/2013 | Glukhovsky |
| 8,377,044 B2 | 2/2013 | Coe et al. |
| 8,382,754 B2 | 2/2013 | Odom et al. |
| 8,403,916 B2 | 3/2013 | Prescott |
| 8,409,076 B2 | 4/2013 | Pang et al. |
| 8,480,668 B2 | 7/2013 | Fernandez et al. |
| 8,491,626 B2 | 7/2013 | Roy et al. |
| 8,517,931 B2 | 8/2013 | Minnelli et al. |
| 8,518,057 B2 | 8/2013 | Walberg et al. |
| 8,556,919 B2 | 10/2013 | Aguirre et al. |
| 8,579,787 B2 | 11/2013 | Shapiro et al. |
| 8,585,685 B2 | 11/2013 | Hagg |
| 8,602,981 B2 | 12/2013 | Deutch |
| 8,608,773 B2 | 12/2013 | Tierney et al. |
| 8,623,011 B2 | 1/2014 | Spivey |
| 8,628,529 B2 | 1/2014 | Aldridge et al. |
| 8,636,762 B2 | 1/2014 | Whitman et al. |
| 8,637,818 B2 | 1/2014 | Balakin |
| 8,685,043 B2 | 4/2014 | Jugenheimer et al. |
| 8,758,394 B2 | 6/2014 | Zimmerling et al. |
| 8,764,769 B1 | 7/2014 | Rodriguez-Navarro et al. |
| 8,790,245 B2 | 7/2014 | Rodriguez Fernandez et al. |
| 8,820,602 B2 | 9/2014 | Walberg et al. |
| 8,827,891 B2 | 9/2014 | Roberts |
| 8,828,024 B2 | 9/2014 | Farritor et al. |
| 8,894,574 B2 | 11/2014 | Ellman |
| 8,926,656 B2 | 1/2015 | Palermo et al. |
| 8,944,997 B2 | 2/2015 | Fernandez et al. |
| 8,968,332 B2 | 3/2015 | Farritor et al. |
| 8,968,356 B2 | 3/2015 | Mueller |
| 9,011,468 B2 | 4/2015 | Ketai et al. |
| 9,033,957 B2 | 5/2015 | Cadeddu et al. |
| 9,044,256 B2 | 6/2015 | Cadeddu et al. |
| 9,339,285 B2 | 5/2016 | Rodriguez-Navarro et al. |
| 9,386,973 B2 | 7/2016 | Deutch |
| 9,561,031 B2 | 2/2017 | Heinrich et al. |
| 9,627,120 B2 | 4/2017 | Scott et al. |
| 9,844,391 B2 | 12/2017 | Rodriguez Fernandez et al. |
| 9,962,148 B2 | 5/2018 | Deutch |
| 9,974,546 B2 | 5/2018 | Rodriguez Fernandez et al. |
| 10,010,370 B2 | 7/2018 | Rodriguez-Navarro et al. |
| 10,130,381 B2 | 11/2018 | Rodriguez-Navarro et al. |
| 10,143,459 B2 | 12/2018 | Heftman |
| 10,335,134 B2 | 7/2019 | Deutch |
| 10,537,348 B2 | 1/2020 | Rodriguez-Navarro et al. |
| 10,905,511 B2 | 2/2021 | Rodriguez-Navarro et al. |
| 11,020,137 B2 | 6/2021 | Rodriguez-Navarro |
| 2001/0038683 A1 | 11/2001 | Ritter et al. |
| 2002/0100486 A1 | 8/2002 | Creighton, IV et al. |
| 2002/0107533 A1 | 8/2002 | Solingen |
| 2002/0116043 A1 | 8/2002 | Garibaldi et al. |
| 2002/0173805 A1 | 11/2002 | Matsuno et al. |
| 2003/0114731 A1 | 6/2003 | Cadeddu et al. |
| 2003/0125752 A1 | 7/2003 | Werp et al. |
| 2003/0181945 A1 | 9/2003 | Opolski et al. |
| 2003/0208185 A1 | 11/2003 | Sheffer et al. |
| 2004/0044295 A1 | 3/2004 | Reinert et al. |
| 2004/0050395 A1 | 3/2004 | Ueda et al. |
| 2004/0064153 A1 | 4/2004 | Creighton, IV et al. |
| 2004/0068173 A1 | 4/2004 | Viswanathan |
| 2004/0158972 A1 | 8/2004 | Creighton, IV et al. |
| 2004/0172057 A1 | 9/2004 | Guillebon et al. |
| 2004/0186347 A1 | 9/2004 | Shose et al. |
| 2004/0199074 A1 | 10/2004 | Ritter et al. |
| 2004/0230100 A1 | 11/2004 | Shluzas |
| 2004/0249262 A1 | 12/2004 | Werp et al. |
| 2005/0080440 A1 | 4/2005 | Durgin et al. |
| 2005/0085696 A1 | 4/2005 | Uchiyama et al. |
| 2005/0113628 A1 | 5/2005 | Creighton, IV et al. |
| 2005/0131390 A1 | 6/2005 | Heinrich et al. |
| 2005/0165449 A1 | 7/2005 | Cadeddu et al. |
| 2005/0220583 A1 | 10/2005 | Lutz |
| 2005/0250988 A1 | 11/2005 | Ewers et al. |
| 2005/0277975 A1 | 12/2005 | Saadat et al. |
| 2006/0015178 A1 | 1/2006 | Moaddeb et al. |
| 2006/0074448 A1 | 4/2006 | Harrison et al. |
| 2006/0079897 A1 | 4/2006 | Harrison et al. |
| 2006/0089633 A1 | 4/2006 | Bleich et al. |
| 2006/0116714 A1 | 6/2006 | Sepetka et al. |
| 2006/0149135 A1 | 7/2006 | Paz |
| 2006/0152309 A1 | 7/2006 | Mintchev et al. |
| 2006/0228421 A1 | 10/2006 | Seeney et al. |
| 2006/0241691 A1 | 10/2006 | Wilk |
| 2006/0247522 A1 | 11/2006 | Megee |
| 2006/0276738 A1 | 12/2006 | Becker |
| 2006/0293566 A1 | 12/2006 | Brown |
| 2007/0004958 A1 | 1/2007 | Ohdaira |
| 2007/0016010 A1 | 1/2007 | Creighton, IV et al. |
| 2007/0027458 A1 | 2/2007 | Sixto, Jr. et al. |
| 2007/0043359 A1 | 2/2007 | Altarac et al. |
| 2007/0073102 A1 | 3/2007 | Matsuno et al. |
| 2007/0135678 A1 | 6/2007 | Suzuki |
| 2007/0135685 A1 | 6/2007 | Cuschieri |
| 2007/0135802 A1 | 6/2007 | Suzuki |
| 2007/0135803 A1 | 6/2007 | Belson |
| 2007/0156028 A1 | 7/2007 | Van Lue et al. |
| 2007/0191670 A1 | 8/2007 | Spector |
| 2007/0221233 A1 | 9/2007 | Kawano et al. |
| 2007/0255273 A1 | 11/2007 | Fernandez et al. |
| 2007/0270629 A1 | 11/2007 | Charles |
| 2007/0282311 A1 | 12/2007 | Scott et al. |
| 2008/0081883 A1 | 4/2008 | King, II et al. |
| 2008/0097496 A1* | 4/2008 | Chang ................ A61B 17/064 606/157 |
| 2008/0108860 A1 | 5/2008 | Bell et al. |
| 2008/0134474 A1 | 6/2008 | Uryasov |
| 2008/0171907 A1 | 7/2008 | Long et al. |
| 2008/0243106 A1 | 10/2008 | Coe et al. |
| 2008/0249534 A1 | 10/2008 | Gruber et al. |
| 2008/0269779 A1 | 10/2008 | Cadeddu et al. |
| 2008/0300458 A1 | 12/2008 | Kim et al. |
| 2009/0005636 A1 | 1/2009 | Pang et al. |

(56) References Cited

U.S. PATENT DOCUMENTS

| | | |
|---|---|---|
| 2009/0004324 A1 | 2/2009 | Dominguez et al. |
| 2009/0043246 A1 | 2/2009 | Dominguez |
| 2009/0054909 A1 | 2/2009 | Farritor et al. |
| 2009/0062772 A1 | 3/2009 | Wakeford et al. |
| 2009/0076536 A1 | 3/2009 | Rentschler et al. |
| 2009/0137984 A1 | 5/2009 | Minnelli |
| 2009/0187074 A1 | 7/2009 | Saadat et al. |
| 2009/0192344 A1 | 7/2009 | Bakos et al. |
| 2009/0026771 A1 | 10/2009 | Baskett |
| 2009/0267717 A1 | 10/2009 | Baskett |
| 2009/0318762 A1 | 12/2009 | Segawa et al. |
| 2010/0030026 A1 | 2/2010 | Uchiyama et al. |
| 2010/0036394 A1 | 2/2010 | Mintz et al. |
| 2010/0036399 A1 | 2/2010 | Viola |
| 2010/0081876 A1 | 4/2010 | Linenkugel et al. |
| 2010/0105984 A1 | 4/2010 | Brewer et al. |
| 2010/0113872 A1 | 5/2010 | Asada et al. |
| 2010/0114126 A1 | 5/2010 | Neff |
| 2010/0137845 A1 | 6/2010 | Ramstein et al. |
| 2010/0145147 A1 | 6/2010 | Pinsky et al. |
| 2010/0152539 A1 | 6/2010 | Ghabrial et al. |
| 2010/0160739 A1 | 6/2010 | Van Lue |
| 2010/0168523 A1 | 7/2010 | Ducharme |
| 2010/0174234 A1 | 7/2010 | Werp et al. |
| 2010/0193566 A1 | 8/2010 | Scheib et al. |
| 2010/0204727 A1 | 8/2010 | Dominguez |
| 2010/0217245 A1 | 8/2010 | Prescott |
| 2010/0237206 A1 | 9/2010 | Barker |
| 2010/0256636 A1 | 10/2010 | Fernandez et al. |
| 2010/0268254 A1 | 10/2010 | Golden et al. |
| 2010/0298645 A1 | 11/2010 | Deutch |
| 2011/0040152 A1 | 2/2011 | Kim et al. |
| 2011/0054306 A1 | 3/2011 | Del Nido et al. |
| 2011/0087223 A1 | 4/2011 | Spivey |
| 2011/0087224 A1 | 4/2011 | Cadeddu et al. |
| 2011/0087249 A1 | 4/2011 | Rodrigues et al. |
| 2011/0105848 A1 | 5/2011 | Sadovsky et al. |
| 2011/0121050 A1 | 5/2011 | Nicholas et al. |
| 2011/0130787 A1 | 6/2011 | Cinquin et al. |
| 2011/0184440 A1 | 7/2011 | Saldinger |
| 2011/0230726 A1 | 9/2011 | Viola |
| 2011/0276941 A1 | 11/2011 | Oi |
| 2011/0283822 A1 | 11/2011 | Cadeddu et al. |
| 2011/0284014 A1 | 11/2011 | Cadeddu et al. |
| 2011/0285488 A1 | 11/2011 | Scott et al. |
| 2011/0295067 A1 | 12/2011 | Rodriguez Fernandez et al. |
| 2011/0306840 A1 | 12/2011 | Allen et al. |
| 2011/0313415 A1 | 12/2011 | Fernandez et al. |
| 2012/0016362 A1 | 1/2012 | Heinrich et al. |
| 2012/0035416 A1 | 2/2012 | Fernandez et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078292 A1 | 3/2012 | Banju |
| 2012/0008535 A1 | 4/2012 | Cadeddu et al. |
| 2012/0085358 A1 | 4/2012 | Cadeddu et al. |
| 2012/0101488 A1 | 4/2012 | Aldridge et al. |
| 2012/0116148 A1 | 5/2012 | Weinberg et al. |
| 2012/0227748 A1 | 9/2012 | Sanders |
| 2012/0238796 A1 | 9/2012 | Conlon |
| 2012/0330089 A1 | 12/2012 | Ritter et al. |
| 2013/0030462 A1 | 1/2013 | Keating et al. |
| 2013/0066304 A1 | 3/2013 | Belson et al. |
| 2013/0085341 A1 | 4/2013 | Nobis et al. |
| 2013/0090666 A1 | 4/2013 | Hess et al. |
| 2013/0109267 A1 | 5/2013 | Schweikardt et al. |
| 2013/0110128 A1 | 5/2013 | Schostek et al. |
| 2013/0123828 A1 | 5/2013 | Culmer et al. |
| 2013/0158348 A1 | 6/2013 | Nobis et al. |
| 2013/0158523 A1 | 6/2013 | Bergs et al. |
| 2013/0158659 A1 | 6/2013 | Bergs et al. |
| 2013/0158660 A1 | 6/2013 | Bergs et al. |
| 2013/0172672 A1 | 7/2013 | Iddan et al. |
| 2013/0172906 A1 | 7/2013 | Olson et al. |
| 2013/0226226 A1 | 8/2013 | Garrison et al. |
| 2013/0245356 A1 | 9/2013 | Fernandez et al. |
| 2013/0253256 A1 | 9/2013 | Griffith et al. |
| 2013/0253275 A1 | 9/2013 | Ransden et al. |
| 2013/0253550 A1 | 9/2013 | Beisel et al. |
| 2013/0267788 A1 | 10/2013 | Duan et al. |
| 2013/0289579 A1 | 10/2013 | Yeung et al. |
| 2013/0289768 A1 | 10/2013 | Yeung et al. |
| 2013/0303851 A1 | 11/2013 | Griffith et al. |
| 2014/0066695 A1 | 3/2014 | Deutch |
| 2014/0084761 A1 | 3/2014 | Scott et al. |
| 2014/0135616 A1 | 5/2014 | Stein et al. |
| 2014/0176797 A1 | 6/2014 | Silva et al. |
| 2014/0187857 A1 | 7/2014 | Wilson et al. |
| 2014/0243586 A1 | 8/2014 | Rohaninejad et al. |
| 2014/0243597 A1 | 8/2014 | Weisenburgh, II et al. |
| 2014/0257370 A1 | 9/2014 | Taylor et al. |
| 2014/0276335 A1 | 9/2014 | Pate |
| 2014/0277104 A1 | 9/2014 | Rodriguez-Navarro et al. |
| 2014/0350574 A1 | 11/2014 | Farritor et al. |
| 2014/0358229 A1 | 12/2014 | Bergs et al. |
| 2015/0012010 A1 | 1/2015 | Adler et al. |
| 2016/0038135 A1 | 2/2016 | Deutch |
| 2016/0120613 A1 | 5/2016 | Cadeddu et al. |
| 2016/0228138 A1 | 8/2016 | Rodriguez-Navarro et al. |
| 2016/0302811 A1 | 10/2016 | Rodriguez-Navarro et al. |
| 2018/0092703 A1 | 4/2018 | Rodriguez-Navarro et al. |
| 2018/0153633 A1 | 6/2018 | Rodriguez-Navarro et al. |
| 2018/0271550 A1 | 9/2018 | Rodriguez-Navarro |
| 2018/0271603 A1 | 9/2018 | Nir et al. |
| 2018/0296289 A1 | 10/2018 | Rodriguez-Navarro et al. |
| 2018/0325604 A1 | 11/2018 | Atarot et al. |
| 2019/0269394 A1 | 9/2019 | Deutch |
| 2019/0350575 A1 | 11/2019 | Deutch |
| 2020/0289140 A1 | 9/2020 | Rodriguez-Navarro et al. |
| 2021/0290330 A1 | 9/2021 | Rodriguez-Navarro et al. |

FOREIGN PATENT DOCUMENTS

| | | |
|---|---|---|
| CN | 2244381 Y | 1/1997 |
| CN | 101090672 A | 12/2007 |
| CN | 201079412 Y | 7/2008 |
| CN | 201091596 Y | 7/2008 |
| CN | 101534725 A | 9/2009 |
| CN | 102068288 A | 5/2011 |
| CN | 102355865 A | 2/2012 |
| CN | 203953720 U | 11/2014 |
| DE | 19534618 A1 | 3/1997 |
| DE | 10 2005 006 705 A1 | 8/2006 |
| DE | 10-2010-010417 A1 | 9/2011 |
| EP | 1 797 823 A1 | 6/2007 |
| EP | 1 972 284 A2 | 9/2008 |
| EP | 2 012 697 A2 | 1/2009 |
| EP | 2 355 699 A2 | 8/2011 |
| EP | 2 366 357 A1 | 9/2011 |
| EP | 2 381 873 A2 | 11/2011 |
| EP | 2 391 277 | 12/2011 |
| EP | 1 942 810 B1 | 8/2012 |
| EP | 2 571 443 A2 | 3/2013 |
| EP | 2 595 548 | 5/2013 |
| EP | 2 842 511 A1 | 3/2015 |
| JP | 09-192137 A | 7/1997 |
| JP | 2004-357816 A | 12/2004 |
| JP | 2005-021576 A | 1/2005 |
| JP | 4320214 B2 | 8/2009 |
| JP | 2009-538699 A | 11/2009 |
| WO | WO-00/51500 A1 | 9/2000 |
| WO | WO-2005/004734 A1 | 1/2005 |
| WO | WO-2005/032370 A1 | 4/2005 |
| WO | WO-2006/071120 A1 | 7/2006 |
| WO | WO-2007/067231 A1 | 6/2007 |
| WO | WO-2007/130382 A2 | 11/2007 |
| WO | WO-2007/130382 A3 | 11/2007 |
| WO | WO-2007/142977 A2 | 12/2007 |
| WO | WO-2007/142977 A3 | 12/2007 |
| WO | WO-2007/143162 A2 | 12/2007 |
| WO | WO-2007/143162 A3 | 12/2007 |
| WO | WO-2007/143170 A2 | 12/2007 |
| WO | WO-2007/143170 A3 | 12/2007 |
| WO | WO-2008/039237 A1 | 4/2008 |

(56) References Cited

FOREIGN PATENT DOCUMENTS

| WO | WO-2008/085919 A2 | 7/2008 |
|---|---|---|
| WO | WO-2008/085919 A3 | 7/2008 |
| WO | WO-2008/131128 A1 | 10/2008 |
| WO | WO-2009/008865 A1 | 1/2009 |
| WO | WO-2009/019288 A2 | 2/2009 |
| WO | WO-2009/019288 A3 | 2/2009 |
| WO | WO-2009/070743 A1 | 6/2009 |
| WO | WO-2010/056716 A2 | 5/2010 |
| WO | WO-2010/056716 A3 | 5/2010 |
| WO | WO-2010/077561 A1 | 7/2010 |
| WO | WO-2010/083480 A2 | 7/2010 |
| WO | WO-2010/083480 A3 | 7/2010 |
| WO | WO-2010/089635 A1 | 8/2010 |
| WO | WO-2011/044468 A2 | 4/2011 |
| WO | WO-2011/044468 A3 | 4/2011 |
| WO | WO-2011/044471 A2 | 4/2011 |
| WO | WO-2011/044471 A3 | 4/2011 |
| WO | WO-2011/091483 A1 | 8/2011 |
| WO | WO-2011/146691 A2 | 11/2011 |
| WO | WO-2011/146691 A3 | 11/2011 |
| WO | WO2011/146698 A2 | 11/2011 |
| WO | WO2011/146698 A3 | 11/2011 |
| WO | WO-2011/146709 A2 | 11/2011 |
| WO | WO-2011/146709 A3 | 11/2011 |
| WO | WO-2012/010910 A1 | 1/2012 |
| WO | WO-2012/031114 A2 | 3/2012 |
| WO | WO-2012/031114 A3 | 3/2012 |
| WO | WO-2012/033925 A1 | 3/2012 |
| WO | WO-2012/048102 A2 | 4/2012 |
| WO | WO-2012/048102 A3 | 4/2012 |
| WO | WO-2013/096470 A1 | 6/2013 |
| WO | WO-2014/133751 A1 | 9/2014 |
| WO | WO-2014/159023 A1 | 10/2014 |
| WO | WO-2014/163872 A1 | 10/2014 |
| WO | WO-2015/112645 A1 | 7/2015 |
| WO | WO-2015/142953 A1 | 9/2015 |
| WO | WO-2016/168380 A1 | 10/2016 |

OTHER PUBLICATIONS

Final Office Action dated Feb. 26, 2019, for U.S. Appl. No. 15/195,898, filed Jun. 28, 2016, 9 pages.
International Search Report dated Apr. 3, 2017, for PCT Application No. PCT/US2017/012628, filed on Jan. 6, 2017, 2 pages.
Non-Final Office Action dated Sep. 17, 2019, for U.S. Appl. No. 15/728,297, filed Oct. 9, 2017, 8 pages.
Notice of Allowance dated Sep. 11, 2019, for U.S. Appl. No. 15/195,898, filed Jun. 28, 2016, 9 pages.
Notice of Allowance dated Nov. 26, 2019, for U.S. Appl. No. 15/195,898, filed Jun. 28, 2016, 6 pages.
Written Opinion of the International Searching Authority dated Apr. 3, 2017, for PCT Application No. PCT/US2017/012628, filed on Jan. 6, 2017, 7 pages.
Dominguez (2007). "Colecistectomia con un trocar asistida por imanes de neodimio. Reporte de un caso." *Asociacion Mexicana de Cirugia Endo*. vol. 8. No. 4, pp. 172-176 (with English Abstract).
Extended European Search Report dated Jul. 20, 2016, for EP Application No. 14 778 895.4, filed on Feb. 25, 2014, 7 pages.
Extended European Search Report dated Dec. 20, 2016, for EP Application No. 09 839 564.3, filed on Oct. 1, 2009. 11 pages.
Extended European Search Report dated Sep. 27, 2017, for EP Application No. 15 741 055.6, filed on Jan. 21, 2015, 9 pages.
Extended European Search Report dated Oct. 30, 2018, for EP Application No. 16 780 691.8, filed on Apr. 13, 2016, 6 pages.
Extended European Search Report dated Nov. 26, 2018, for EP Application No. 16 780 688.4, filed on Sep. 26, 2017, 9 pages.
Final Office Action dated Sep. 16, 2016, for U.S. Appl. No. 14/704,828, filed May 5, 2015, 10 pages.
Final Office Action dated Jan. 25, 2016, for U.S. Appl. No. 14/337,082, filed Jul. 21, 2014, 9 pages.
Final Office Action dated Dec. 28, 2016, for U.S. Appl. No. 14/200,302, filed Mar. 7, 2014, 15 pages.
Final Office Action dated Sep. 6, 2017, for U.S. Appl. No. 14/200,302, filed Mar. 7, 2014, 9 pages.
Final Office Action dated Mar. 7, 2018, for U.S. Appl. No. 15/098,262, filed Apr. 13, 2016, 10 pages.
International Search Report dated Jul. 30. 2014, for PCT Application No. PCT/US2014/021537, filed on Mar. 7, 2014, 2 pages.
International Search Report for International Application No. PCT/IB2009/054307 dated Feb. 8, 2010, 4 pages.
International Search Report dated May 4, 2015, for PCT Application No. PCT/US2015/012319, filed on Jan. 21, 2015, 2 pages.
International Search Report dated Jul. 18, 2014, for PCT Application No. PCT/US2014/018307, filed on Feb. 25, 2014, 4 pages.
International Search Report dated Jul. 15, 2016, for PCT Application No. PCT/US2016/027385, filed on Apr. 13, 2016, 2 pages.
International Search Report dated Aug. 22, 2016, for PCT Application No. PCT/US2016/027390, filed on Apr. 13, 2016, 4 pages.
Non-Final Office Action dated May 25, 2016, for U.S. Appl. No. 14/200,302, filed Mar. 7, 2014, 12 pages.
Non-Final Office Action dated May 21, 2013 for U.S. Appl. No. 13/132,185, filed Aug. 17, 2011, 18 pages.
Non-Final Office Action dated Jul. 21, 2016, for U.S. Appl. No. 14/337,082, filed Jul. 21, 2014, 9 pages.
Non-Final Office Action dated Jul. 13, 2015, for U.S. Appl. No. 14/337,082, filed Jul. 21, 2014, 10 pages.
Non-Final Office Action dated Jan. 25, 2016, for U.S. Appl. No. 14/704,828, filed May 5, 2015, 9 pages.
Non-Final Office Action dated Jul. 14, 2015, for U.S. Appl. No. 14/704,828, filed May 5, 2015, 10 pages.
Non-Final Office Action dated Oct. 24, 2013, for U.S. Appl. No. 14/019,370, filed Sep. 5, 2013, 7 pages.
Non-Final Office Action dated Oct. 22, 2015, for U.S. Appl. No. 14/019,404, filed Sep. 5, 2013, 6 pages.
Non-Final Office Action dated May 22, 2017, for U.S. Appl. No. 14/200,302, filed Mar. 7, 2014, 14 pages.
Non-Final Office Action dated May 3, 2017, for U.S. Appl. No. 14/704,828, filed May 5, 2015, 8 pages.
Non-Final Office Action dated Jul. 24, 2017, for U.S. Appl. No. 15/098,262, filed Apr. 13, 2016, 9 pages.
Non-Final Office Action dated Jun. 29, 2018, for U.S. Appl. No. 15/195,898, filed Jun. 28, 2016, 9 pages.
Notice of Allowance dated Feb. 14, 2014, for U.S. Appl. No. 14/019,370, filed Sep. 5, 2013, 7 pages.
Notice of Allowance dated Mar. 14, 2014, for U.S. Appl. No. 13/132,185, filed Aug. 17, 2011, 7 pages.
Notice of Allowance dated Mar. 14, 2016, for U.S. Appl. No. 14/019,404, filed Sep. 5, 2013, 7 pages.
Notice of Allowance dated May 3, 2017, for U.S. Appl. No. 14/337,082, filed Jul. 21, 2014, 7 pages.
Notice of Allowance dated Aug. 25, 2017, for U.S. Appl. No. 14/337,082, filed Jul. 21, 2014, 7 pages.
Notice of Allowance dated Nov. 22, 2017, for U.S. Appl. No. 14/200,302, filed Mar. 7, 2014, 5 pages.
Notice of Allowance dated Jan. 19, 2018, for U.S. Appl. No. 14/704,828, filed May 5, 2015, 7 pages.
Notice of Allowance dated Aug. 24, 2018, for U.S. Appl. No. 15/098,262, filed Apr. 13, 2016, 9 pages.
Wikipedia (2015). "Stainless Steel," retrieved from https://en.wikipedia.org/wiki/Stainless_steel, 13 pages.
Written Opinion of the International Searching Authority dated Jul. 30, 2014, for PCT Application No. PCT/US2014/021537, filed on Mar. 7, 2014, 5 pages.
Written Opinion of the international Searching Authority for International Application No. PCT/IB2009/054307 dated Feb. 8, 2010.
Written Opinion of the International Searching Authority dated Jul. 18, 2014, for PCT Application No. PCT/US2014/018307, filed on Feb. 25, 2014, 5 pages.
Written Opinion of the International Searching Authority dated May 4, 2015, for PCT Application No. PCT/US2015/012319, filed on Jan. 21, 2015, 5 pages.

(56) References Cited

OTHER PUBLICATIONS

Written Opinion of the international Searching Authority dated Jul. 15, 2016, for PCT Application No. PCT/US2016/027385, filed on Apr. 13, 2016, 11 pages.
Written Opinion of the International Searching Authority dated Aug. 22, 2016, for PCT Application No. PCT/US2016/027390, filed on Apr. 13, 2016, 9 pages.
Best, S.L. et al. (2010). "Development of magnetic anchoring and guidance systems for minimally invasive surgery," Indian J. of Urology 26:418-422.
Best, S.L. et al. (2010). "Solo Surgeon LESS Nephrectomy Facilitated by New Generation Magnetically Anchored and Guided (MAGS) Camera," World Congress of Endourology, PS38-14, Chicago IL, Sep. 2010.
Best, S.L. et al. (2010). "MAGS Instrumentation for LESS/NOTES: Lack of Histologic Damage After Prolonged Magnetic Coupling Across the Abdominal Wall," World Congress of Endourology, PS2-4, Chicago IL, Sep. 2010.
Best, S.L. et al. (2008). "Maximizing Coupling Strength of Magnetically Anchored NOTES Instruments: How Thick Can We Go?" Surgical Endoscopy, vol. 22: S241.
Cadeddu, J.A. et al. (2002). "Transabdominal magnetic anchoring system for trocar-less laparoscopic surgery," J. of Urology, vol. 167, No. 4, Supplement, Abstract No. 16, 1 total page.
Cadeddu, J et al. (2009). "Novel Magnetically Guided Intraabdominal Camera to Facilitate Laparoendoscopic Single Site Surgery: Initial Human Experience," Surgical Endoscopy 23:1894-1899.
Dominguez, G. et al. (2009). "Retraction and triangulation with neodymium magnetic forceps for single-port laparoscopic cholecystectomy," Surg. Endosc. 23:1660-1666.
Duchene, D.A. et al. (2004). "Magnetic positioning system for trocarless laparoscopic instruments," J. of Endourology 18:693.
Fernandez, R. et al. (2012). "Determining a Performance Envelope for Capture of Kidney Stones Functionalized with Superparamagnetic Particles," Journal of Endourology, 26(9):1227-30.
Fernandez, R. et al. (2003). "Development of a Transabdominal Anchoring System for Trocar-Less Laparoscopic Surgery," Advances in Bioengineering—ASME International Mechanical Engineering Congress & Exposition, Washington DC, Nov. 2003, BED vol. 55, pp. 157-158.
Leong, F. et al. (2016). "Magnetic surgical instruments for robotic abdominal surgery," IEEE Reviews in Biomedical Engineering 9:66-78.
Mashaud, L. et al. (2011). "Tissue Compression Analysis for Magnetically Anchored Cautery Dissector During Single Site Laparoscopic Cholecystectomy," Journal of Gastrointestinal Surgery 15:902-907.
Mashaud, L. et al. (2010). "Tissue Compression Analysis for Magnetically Anchored Cautery Dissector During Single Site Laparoscopic Cholecystectomy," Gastroenterology, 138:5 (Supplement 1):S-882.
Mashaud, L. et al. (2010). "Magnetic Cautery Dissector Suitability for Traditional or Single Site Laparoscopic Cholecystectomy in Human Cadaver Models," 12th World Congress of Endoscopic Surgery, p. 246, National Harbor, MD, Apr. 2010.
Non-Final Office Action dated Mar. 3, 2020, for U.S. Appl. No. 15/728,302, filed Oct. 9, 2017, 14 pages.
Non-Final Office Action dated Mar. 6, 2020, for U.S. Appl. No. 15/926,578, filed Mar. 20, 2018, 9 pages.
Park, S. et al. (2007). "Trocar-less instrumentation for laparoscopy magnetic positioning of intra-abdominal camera and retractor," Surgical Technique 245:379-384.
Raman, J. (2009). "Complete Transvaginal NOTES Nephrectomy Using Magnetically Anchored Instrumentation," Journal of Endourology 23:367-371.
Rivas, H. et al. (2005). "A Magnetic Positioning System to Drive Trocarless Laparoscopic Instruments," First International Minimally Invasive Robotic Association (MIRA) Conference on Robotic Surgery, Innsbruck, Austria, Dec. 2005.
Scott, D.J. et al. (2007). "Completely transvaginal NOTES cholecystectomy using magnetically anchored instruments," Surg. Endosc. 21:2308-2316.
Scott, D. et al. (2008). "Optimizing Magnetically Anchored Camera, Light Source, Graspers, and Cautery Dissector for Transvaginal NOTES Cholecystectomy," Surgical Endoscopy 22:S244.
Scott, D. et al. (2008). "A Randomized Comparison of Laparoscopic, Flexible Endoscopic, and Wired and Wireless Magnetic NOTES Cameras on Ex-Vivo and In-Vivo Surgical Performance," Gastrointestinal Endoscopy, vol. 67: AB115.
Scott, D. et al. (2008). "Transvaginal Single Access "Pure" NOTES Sleeve Gastrectomy Using a Deployable Magnetically Anchored Video Camera," Gastrointestinal Endoscopy, vol. 67: AB116.
Scott, D. et al. (2007). "Transgastric, Transcolonic, and Transvaginal Cholecystectomy Using Magnetically Anchored Instruments," Surgical Endoscopy, vol. 21: S474.
Scott, D. et al. (2007). "Completely Transvaginal Cholecystectomy Using Magnetically Anchored Instruments," Surgical Endoscopy, vol. 21: S335.
Scott, D. et al. (2007). "Short-Term Survival Outcomes Following Transvaginal NOTES Cholecystectomy Using Magnetically Anchored Instruments," Gastrointestinal Endoscopy, vol. 65: AB109.
Swain, C. et al. (2008). "Linear Stapler Formation of Ileo-Rectal, Entero-Enteral and Gastrojejunal Anastomoses During Dual and Single Access "Pure" NOTES Procedures: Methods, Magnets and Stapler Modifications," Gastrointestinal Endoscopy, vol. 67: AB119.
Swain, P. et al. (2008). "Wireless Endosurgery for NOTES," Gastrointestinal Endoscopy, vol. 67: AB104.
Tan, Y. (2011). "Modeling of Magnetic Tools for Use with Superparamagnetic Particles for Magnetic Stone Extraction," 26th Engineering & Urology Society Annual Meeting, p. 29, Washington DC, May 14, 2011.
Tan, Y. (2012). "In Vitro Comparison of Prototype Magnetic Tool with Conventional Nitinol Basket for Ureteroscopic Retrieval of Stone Fragments Rendered Paramagnetic with Iron-Oxide Microparticles," The Journal of Urology, vol. 187, Issue 4, pp. e857-e858.
Tang, S. (2008). "Live Video Manipulator for Endoscopy and NOTES," Gastrointestinal Endoscopy 68:559-564.
Tillander, H. (1951). "Magnetic guidance of a catheter with articulated steel tip," Acta Radiologica pp. 62-64.
Zeltser, I.S. et al. (2007). "Single trocar laparoscopic nephrectomy using magnetic anchoring and guidance system in the porcine model," J. of Urology 178:1-4.
U.S. Appl. No. 61/113,495, filed Nov. 25, 2008, by Fernandez et al.
Final Office Action dated Nov. 25, 2020, for U.S. Appl. No. 15/728,297, filed Oct. 9, 2017, 11 pages.
Non-Final Office Action dated May 12, 2021, for U.S. Appl. No. 16/008,976, filed Jun. 14, 2018, 15 pages.
Notice of Allowance dated Sep. 29, 2020, for U.S. Appl. No. 15/728,302, filed Oct. 9, 2017, 8 pages.
Notice of Allowance dated Feb. 5, 2021, for U.S. Appl. No. 15/926,578, filed Mar. 20, 2018, 9 pages.
Supplemental Notice of Allowability dated Dec. 18, 2020, for U.S. Appl. No. 15/728,302, filed Oct. 9, 2017, 3 pages.
Aesculap, "Endoscopic Vascular surgery in the pelvic region," B/Braun, Aesculap AG & CO.KG, Catalog, 48 pages, 2006, document can be accessed at https://docplayer.net/22042174-Aesculap-endoscopic-technology-endoscopic-vascular-surgery-in-the-pelvic-region.html.
Extended European Search Report dated May 31, 2013, for EP Application No. 08 853 840.0, filed on Nov. 26, 2008, 11 pages.
Final Office Action dated Oct. 26, 2021, for U.S. Appl. No. 16/419,363, filed May 22, 2019, 7 pages.
Final Office Action dated Oct. 28, 2021, for U.S. Appl. No. 16/528,878, filed Aug. 1, 2019, 8 pages.
International Search Report dated Apr. 9, 2009, for PCT Application No. PCT/US2008/084991, filed on Nov. 26, 2008, 3 pages.
Milki et al. (1998). Vaginal ultrasound probe coverage leakage: implications for patient care, fertility and sterility, American Society for Reproductive Medicine, vol. 69, No. 3.
Non-Final Office Action dated Apr. 29, 2021, for U.S. Appl. No. 16/419,363, filed May 22, 2019, 9 pages.

(56) References Cited

OTHER PUBLICATIONS

Non-Final Office Action dated Apr. 15, 2021, for U.S. Appl. No. 16/528,878, filed Aug. 1, 2019, 6 pages.
Non-Final Office Action dated Sep. 15, 2021, for U.S. Appl. No. 15/728,297, filed Oct. 9, 2017, 11 pages.
Odwin et al. (1990). Prove covers and disinfectants for transvaginal transducers, JDMS, 6:130-135.
Written Opinion of the International Searching Authority dated Apr. 9, 2009, for PCT Application No. PCT/US2008/084991, filed on Nov. 26, 2008, 12 pages.

* cited by examiner

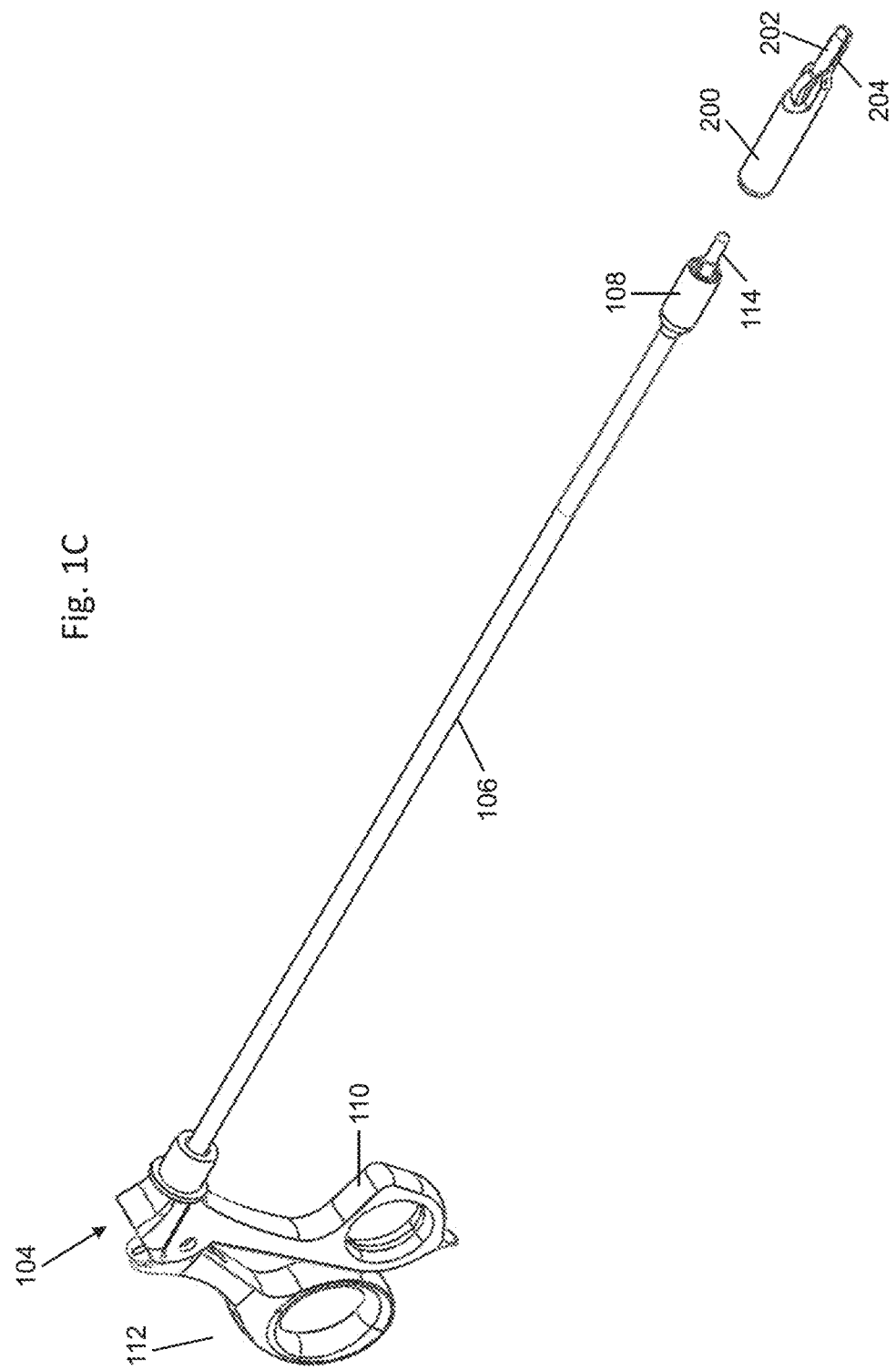

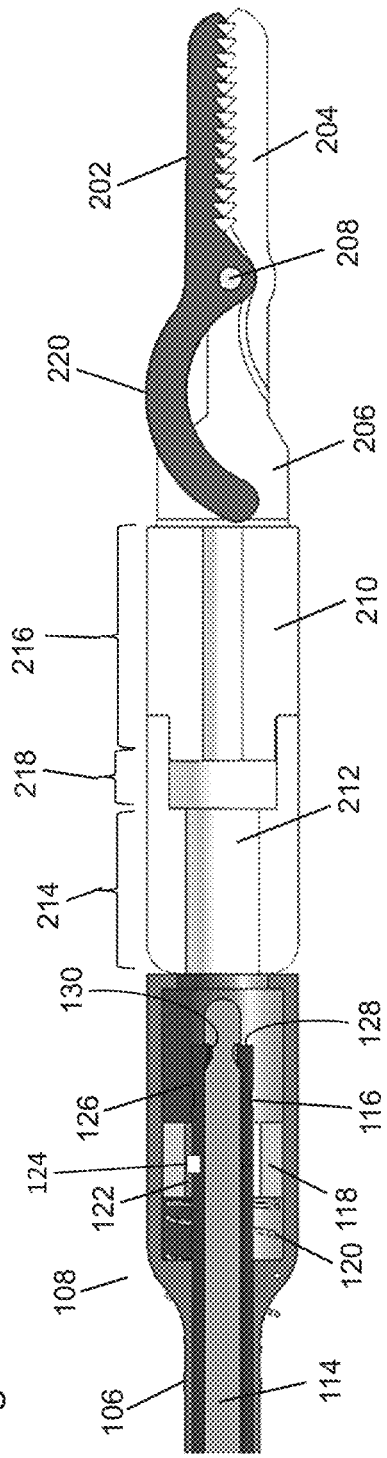
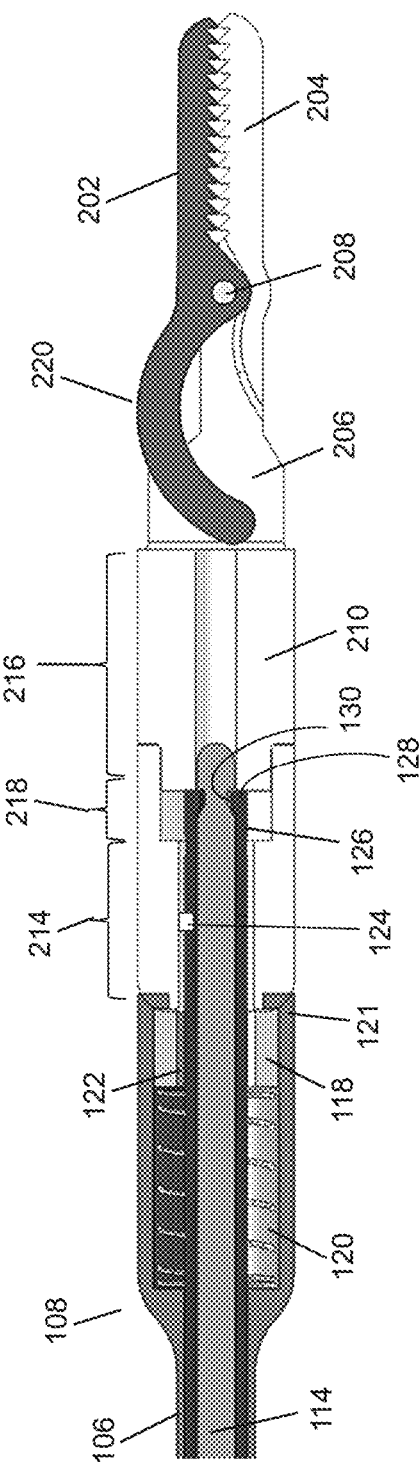
Fig. 2C
Fig. 2D

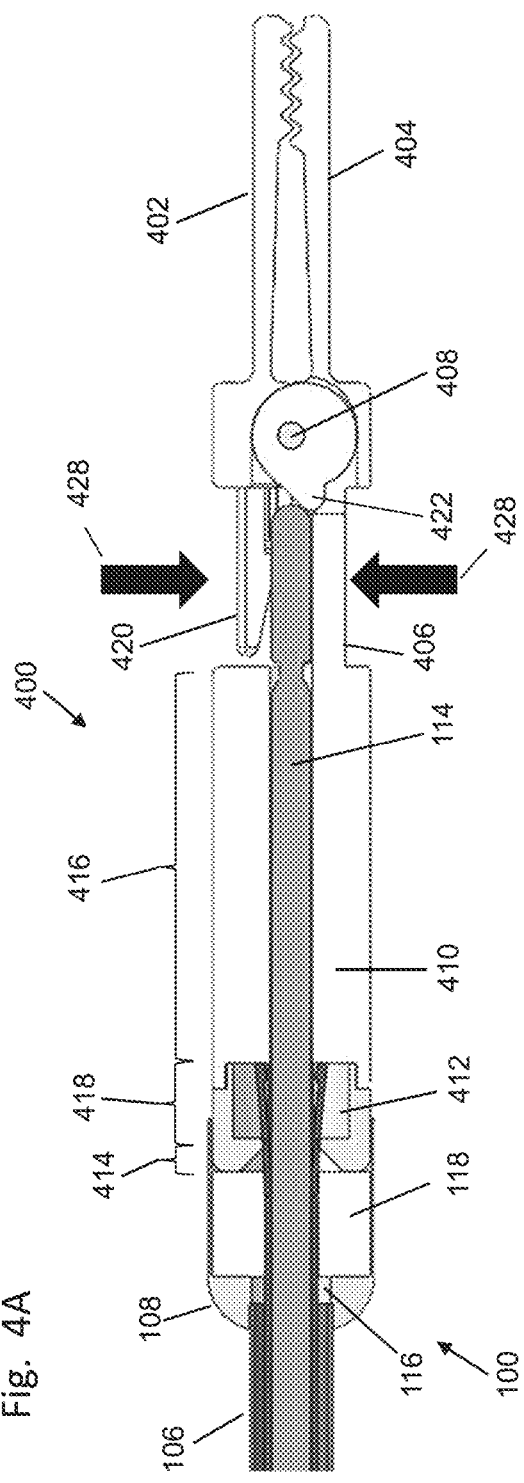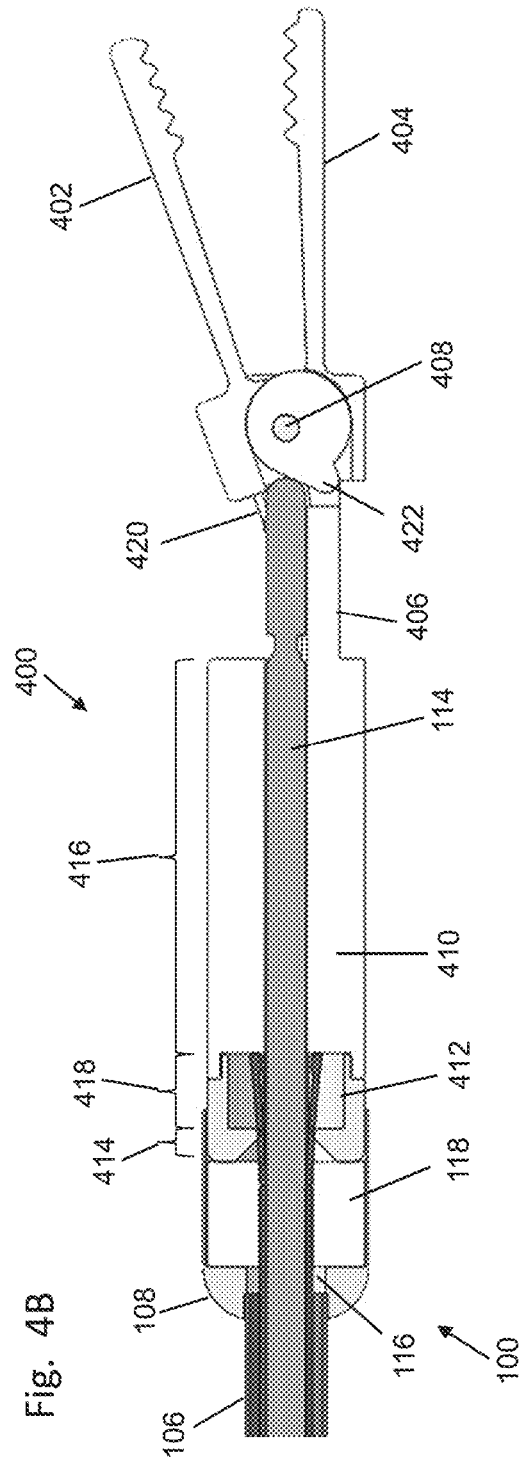

GRASPER WITH MAGNETICALLY-CONTROLLED POSITIONING

CROSS-REFERENCE TO RELATED APPLICATIONS

This application is a continuation of U.S. patent application Ser. No. 15/098,262, filed on Apr. 13, 2016, which issued as U.S. Pat. No. 10,130,381 on Nov. 20, 2018, which is a continuation of U.S. patent application Ser. No. 14/019,404, filed on Sep. 5, 2013, which issued as U.S. Pat. No. 9,339,285 on May 17, 2016, which claims priority to U.S. Provisional Application Ser. No. 61/778,264, filed on Mar. 12, 2013, each of which is hereby incorporated by reference in its entirety.

FIELD

The present invention is directed toward systems, devices, and methods for providing remote manipulation or traction to tissue using one or more graspers.

BACKGROUND

Many surgical procedures are shifting toward the use of minimally-invasive approaches that are configured to minimize the number and size of incisions that are made in a patient. Minimally-invasive procedures such as endoscopic and laparoscopic procedures may be associated with lower pain, quicker post-surgical recovery, shortened hospitalization, and reduced complications when compared to open surgical procedures. During minimally-invasive procedures it may be desirable to reposition or otherwise manipulate tissue, however the introduction of additional devices to engage tissue may crowd the access sites provided by incisions, which may require the formation of larger or additional access sites. Accordingly, it may be desirable to provide one or more devices that may retract or otherwise manipulate tissue without the need to have a portion of the device present in an access site to the body.

BRIEF SUMMARY

Described here are devices, systems, and methods for providing remote traction for tissue. In some variations, the systems described here may comprise a grasping device. The grasping device may comprise a main body comprising a barrel portion having a lumen extending therethrough, a first jaw rotatably coupled to the main body, and a second jaw. The grasper may further comprise a proximal arm extending from the first jaw, wherein at least a portion of the proximal arm is exposed from the main body. The device may be configured such that a one or more forces (e.g., a compressive force or the like) applied to the exposed portion of the proximal arm and the main body rotates the first jaw relative to the second jaw. Additionally or alternatively, the device may be configured such that advancement of an actuation rod through the lumen of the barrel portion rotates the first jaw relative to the second jaw.

In some variations, the lumen of the barrel portion may comprise a proximal segment and distal segment such that a diameter of the proximal segment is larger than a diameter of the distal segment. In some of these variations, the lumen may further comprise an intermediate segment between the proximal segment and the distal segment such that a diameter of the intermediate segment is larger than the diameter of the proximal segment and the diameter of the distal segment. At least a portion of the device may be formed from one or more magnetic or ferromagnetic materials. In some variations, the device may further comprise an eccentric cam member attached to the first jaw such that rotation of the eccentric cam member is configured to rotate the first jaw. The proximal arm may comprise a curved segment. In some of these variations, the proximal arm may further comprise a straight segment positioned between the curved segment and the first jaw. The first jaw may be rotationally biased toward the second jaw.

Also described here are systems for grasping tissue. The system may comprise a grasper and a delivery device. The grasper may comprise a main body comprising a barrel portion having a lumen extending therethrough, a first jaw rotatably coupled to the main body, and a second jaw. The grasper may comprise a proximal arm connected to the first jaw, such that rotation of the proximal arm relative to main body rotates the first jaw away from the second jaw. In some variations, the grasper may further comprise an eccentric cam member attached to the first jaw, wherein rotation of the eccentric cam member is configured to rotate the first jaw. In some of these variations, the proximal arm may comprise a curved segment, and in some of these variations may comprise a straight segment positioned between the curved segment and the first jaw.

The delivery devices described here may comprise a handle, a distal engagement portion configured to releasably couple to the grasper, a shaft connecting the handle and the distal engagement portion, and an actuation rod. The actuation rod may be advanced through the lumen to rotate the first jaw away from the second jaw. In some variations, the delivery device comprises a locking sheath having an expandable distal end. The delivery device may be configured to expand the expandable distal portion from an unexpanded configuration to an expanded configuration in the lumen of the barrel portion to couple the locking sheath to the grasper. In some of these variations, the lumen of the barrel portion may comprise a proximal segment and distal segment, wherein a diameter of the proximal segment is larger than a diameter of the distal segment. The expandable distal portion of the locking sheath may be advanced through the proximal segment in an unexpanded configuration and may be prevented from being advanced through the proximal segment when in the unexpanded configuration.

In some of these variations, the lumen may further comprise an intermediate segment between the proximal segment and the distal segment, wherein a diameter of the intermediate segment is larger than the diameter of the proximal segment and the diameter of the distal segment. The expandable distal portion of the locking sheath may be configured to be expanded in the intermediate section, such that the expandable distal portion of the locking sheath is prevented from being withdrawn through the proximal segment when the expandable distal portion of the locking sheath is expanded. The actuation rod may be positioned within the locking sheath, and may be configured such that advancement of the actuation rod relative to the locking sheath expands the expandable distal portion of the locking sheath. In some of these variations, the expandable distal portion of the locking sheath may comprise at least one internal projection configured to fit in at least on indentation of the actuation rod. Advancement of the actuation rod relative to the locking sheath may slide the at least one internal projection relative to the at least one indentation to expand the expandable distal portion of the locking sheath.

In some variations, the distal engagement portion of the delivery device may comprise a coupling magnet. In some of these variations, retraction of the coupling magnet may decouple the grasper from the distal engagement portion. The retraction of the actuation rod may be configured to retract the coupling magnet. In some variations, the distal engagement portion may comprise a spring (e.g., a torsional spring, a cantilever spring, or the like) positioned to bias the coupling magnet toward an advanced position.

BRIEF DESCRIPTION OF THE DRAWINGS

FIGS. 1A-1C depict perspective views of an illustrative variation of the systems described here.

FIGS. 2A-2F depict cross-sectional side views of a distal portion of a variation of the delivery devices described here and a variation of the graspers described here.

FIGS. 3A, 3B, 4A, and 4B depict cross-sectional side views of illustrative variations of the graspers described here.

DETAILED DESCRIPTION

Figure 1A:
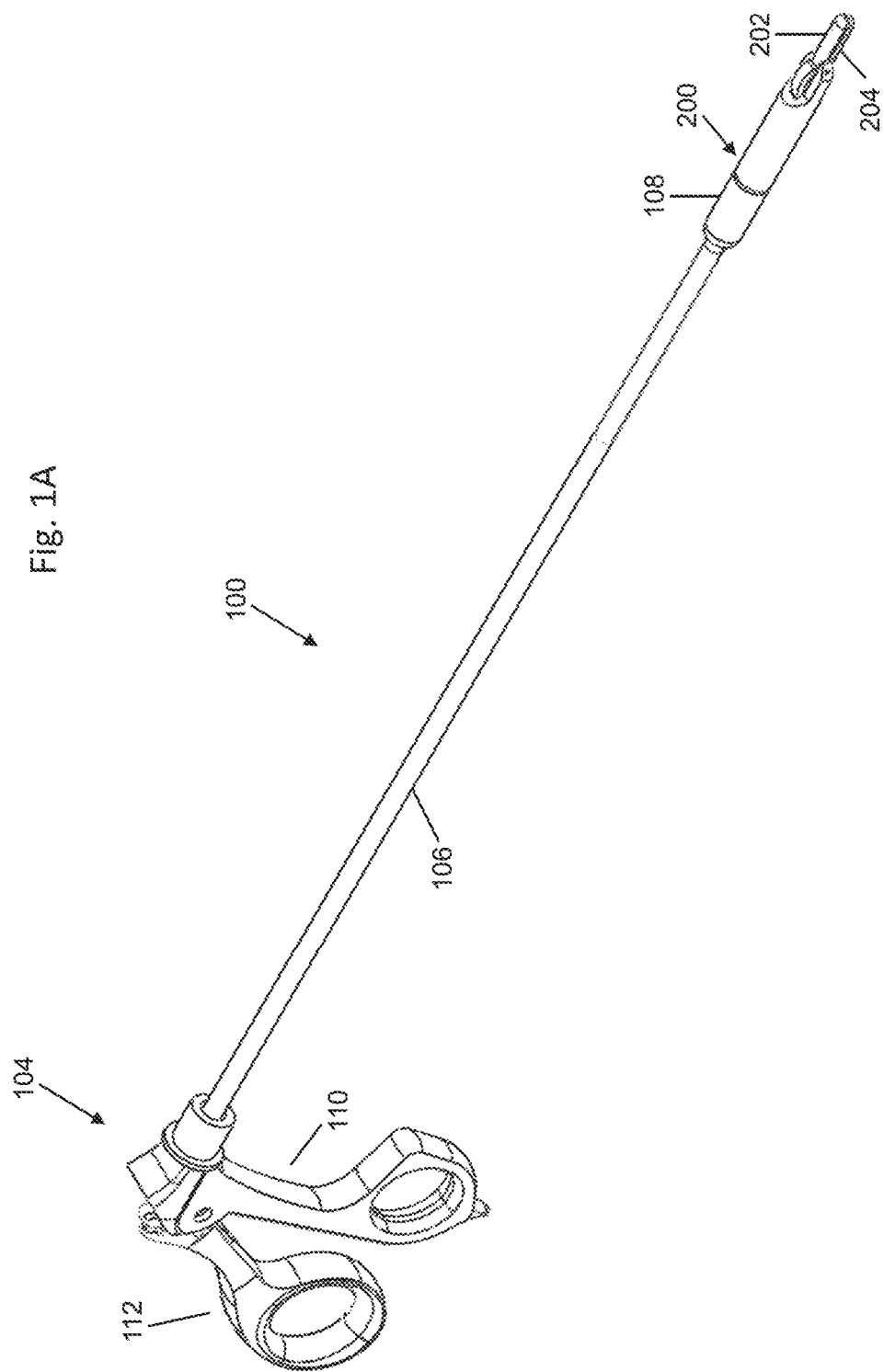

Described here are devices, systems, and methods for providing remote suspension/traction or manipulation of tissue during minimally-invasive procedures. Generally, the systems described here include a grasper that is configured to be releasably connected to tissue. The grasper may be further configured to be attracted to one or more magnets positioned externally of the body to move, reposition, and/or hold the grasper (which may in turn provide traction for the tissue held by the grasper). The systems described here may also comprise a delivery device. The delivery devices described here are generally configured to releasably carry the grasper, and may be further configured to actuate the grasper to selectively connect the grasper to tissue or release the grasper from tissue. The delivery devices are typically further configured to release the grasper from the delivery device (e.g., after the grasper has been connected to tissue). In some instances, the delivery device may be configured to re-couple to the grasper to reposition or remove the grasper. In other instances the system may comprise a separate retrieval device configured to reposition or remove the grasper. In some instances, the delivery device or retrieval device may be used with the grasper to remove tissue from the body. For example, the grasper may be connected to a tissue such as the gall bladder, the tissue may be severed from the body (e.g., using one or more surgical tools), and the grasper may be retrieved using the delivery device or another retrieval device to remove the grasper and tissue from the body.

In some variations, the system may further comprise a magnetic control element (which may include one or more magnets), which may be configured to be positioned outside the body and to provide a magnetic force to the grasper when the grasper is positioned in the body (e.g., to move, reposition, and/or hold the grasper). While illustrative examples of the graspers and delivery devices are described together below, it should be appreciated that any of the graspers described here may be used with any of the delivery devices described here. It should be appreciated that the graspers described here may be actuated and delivered using any suitable delivery device, and that that the delivery devices described here may be used to actuate and deliver any suitable grasper or grasping device.

Generally, the methods described here comprise releasably connecting a grasper (such as one of the graspers described here) to a tissue, and providing a magnetic force to the grasper to move and/or hold the grasper and provide traction of the tissue engaged by the grasper. The magnetic force may be provided by a magnetic control element configured to magnetically attract the grasper. In some variations, the grasper may be releasably connected to a tissue inside of the body, and the magnetic control element may be positioned externally of the body to magnetically attract the grasper. To connect the grasper to the tissue, the grasper may be releasably coupled with a delivery device, wherein the delivery device is configured to actuate the grasper. The delivery device may actuate the grasper to releasably connect the grasper to tissue, and may eject or otherwise decouple from the grasper after the grasper is connected to tissue. When the grasper is decoupled from the delivery device, the grasper may be attracted by an magnetic force external to the body and may move or otherwise hold tissue without the need to have a shaft or other portion of a device positioned in a laparoscopic port or other access site. This may reduce the number of access sites required to provide remote suspension of tissue, which may allow for faster and more reliable surgical procedures. In some instances, the delivery device (or another device, such as a grasping device) may be used to disconnect the grasper from tissue. The grasper may then be repositioned and reattached to tissue (either the same tissue or a different tissue), or may be removed from the body.

Figure 1B:
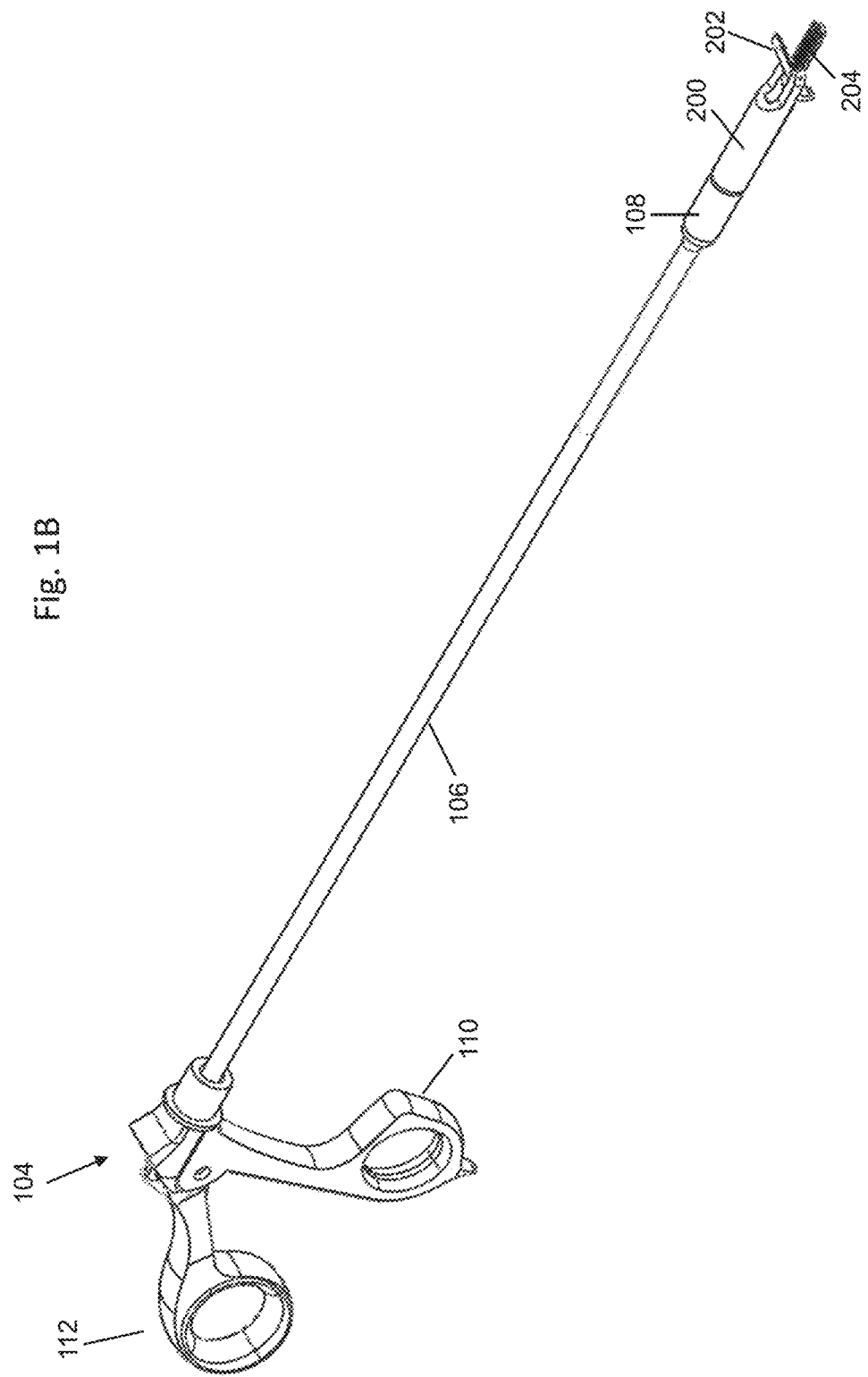

FIGS. 1A-1C depict one variation of the systems described here. Specifically, FIG. 1A shows a perspective view of a system comprising a delivery device (100) and a grasper (200). The grasper may be releasably coupled to the delivery device (100) (as shown in FIGS. 1A and 1B), and may be decoupled from the delivery device (as shown in FIG. 1C). When the grasper (200) is coupled to the delivery device (100), the delivery device (100) may actuate the grasper to connect the grasper to tissue or release the grasper therefrom.

As shown in FIG. 1A, the delivery device (100) may comprise a handle (104), a shaft (106) extending from the handle (104), and a distal engagement portion (108) at a distal end of the shaft (106). In some variations, the delivery device (100) and grasper (200) may be configured for laparoscopic introduction into the body. Accordingly, in some variations the grasper (200) and delivery device (100) may be configured for advancement through a 10 mm laparoscopic port. In these variations, the outer diameter of the grasper may be less than or equal to about 10 mm. Additionally, the delivery device (100) may be configured such that the shaft (106) and the distal engagement portion (108) each have a diameter of less than or equal to about 10 mm. In some of these variations, the distal engagement portion (108) may have an outer diameter of less than or equal to about 10 mm, while the shaft (106) has an outer diameter of less than or equal to about 5 mm. In these variations, it may be possible to advance the distal engagement portion (108) through a 10 mm laparoscopic port, and to further advance a second device having a diameter of about 5 mm or less through the port while the shaft (106) is positioned in the port. It should be appreciated that shaft (106) may have any suitable diameter (e.g., between about 1 mm and about 15 mm, between about 5 mm and about 10 mm, or the like). The shaft (106) and distal engagement portion (108) may be formed from any suitable materials, such as one or more medical-grade, high-strength plastics or metals, such as stainless steel, cobalt chromium, PEEK, one or more nylons, polyimide, or the like.

Generally, the handle (104) comprises an actuation control mechanism that may be manipulated by a user to controllably actuate the grasper. In some variations, the delivery device may comprise a separate decoupling control, which a user may use to decouple the grasper (200) from the delivery device (100). In other variations, the delivery device (100) may be configured such that a user may use the actuation control mechanism to decouple the grasper from the delivery device in addition to actuating the grasper. For example, in the variation of the delivery device (100) depicted in FIGS. 1A-1C, the handle (104) of delivery device (100) may comprise a grip portion (110) and an actuation control mechanism comprising a trigger (112). While shown in FIGS. 1A-1C as being a trigger (112), it should be appreciated that the actuation control mechanism may comprise any suitable control element (e.g., a slider, a knob, or the like) capable of actuating the grasper (200) as described in more detail below. The trigger (112) may be configured to both actuate the grasper (200) and decouple the grasper (200) from the delivery device (100).

Specifically, in some variations the trigger (112) may be moveable between three positions. While three distinct positions will be discussed below, it should be appreciated that the trigger (112) may also assume one or more intermediate positions between these positions. Of the three positions, the trigger may be moveable between a first position (as shown in FIG. 1A) and a second position (as shown in FIG. 1B) to actuate the grasper (200). Specifically, the grasper (200) may comprise a first jaw (202) and a second jaw (204), and at least one of the first jaw (202) and the second jaw (204) may be configured to rotate relative to the grasper (200). The grasper (200) may be actuated between an open configuration and a closed configuration.

In the open configuration, the first jaw (202) and second jaw (204) may be held in rotationally separated positions to define a space between the first jaw (202) and the second jaw (204), as shown in FIG. 1B. In the closed configuration, the first jaw (202) and second jaw (204) may be rotationally biased toward each other, as shown in FIG. 1A. While the first jaw (202) is shown in FIG. 1B as contacting the second jaw (204) when the grasper (200) is in the closed configuration, it should be appreciated that when the grasper (200) is connected to tissue, tissue positioned between the first jaw (202) and second jaw (204) may prevent the first jaw (202) from contacting the second jaw (204) when the grasper (200) is in the closed configuration.

The grasper (200) may be actuated between the closed and open configurations to releasably connect the grasper (200) to tissue. For example, when the trigger (112) is in the first position (as shown in FIG. 1A), the grasper (200) may be placed in the closed configuration. As the trigger (112) is moved to the second position (as shown in FIG. 1B), the grasper (200) may be moved to the open configuration. In variations where the first jaw (202) is configured to rotate relative to the grasper (200), moving the trigger (112) from the first position to the second position may rotate the first jaw (202) away from the second jaw (204), while moving the trigger from the second position back to the first position may rotate the first jaw (202) toward the second jaw (204). Accordingly, by moving the trigger (112) between the first and second positions, a user may selectively open and close the jaws of the grasper (200) using the delivery device (100). To connect the grasper (200) to tissue, a user may place the trigger (112) in the second position (or an intermediate position between the first and second positions) to open (or partially open) the jaws, and may manipulate the delivery device (100) to position tissue between the first jaw (202) and the second jaw (204). With the tissue positioned between the jaws, the trigger (112) may be returned to the first position to clamp the jaws against the tissue, thereby releasably connecting the grasper (200) to the tissue.

As mentioned above, the trigger (112) may be configured to decouple the grasper (200) from the delivery device. For example, the trigger (112) may be moved from the first position (as shown in FIG. 1A) to a third position (as shown in FIG. 1C), and the delivery device (100) may be configured to decouple from the grasping member when the trigger is moved to the third position (as will be described in more detail below). When the same actuation control mechanism is used to actuate the grasper and decouple the grasper from the delivery device, it may be desirable to decouple the grasper from the delivery device when the grasper (200) is in a closed configuration and engaged with tissue. Accordingly, in some variations, the first position of the trigger (112) (which may correspond to a closed configuration of the grasper (200)) may be an intermediate position between the second position and third position. In these variations, when the trigger (112) is placed in the second position to place the grasper (200) in an open configuration, the trigger (112) will move through the first position (which may move the grasper (200) to a closed configuration) before it reaches the third position. Thus the grasper (200) may be moved to the closed configuration before it is decoupled from the delivery device (100).

Figure 2A:
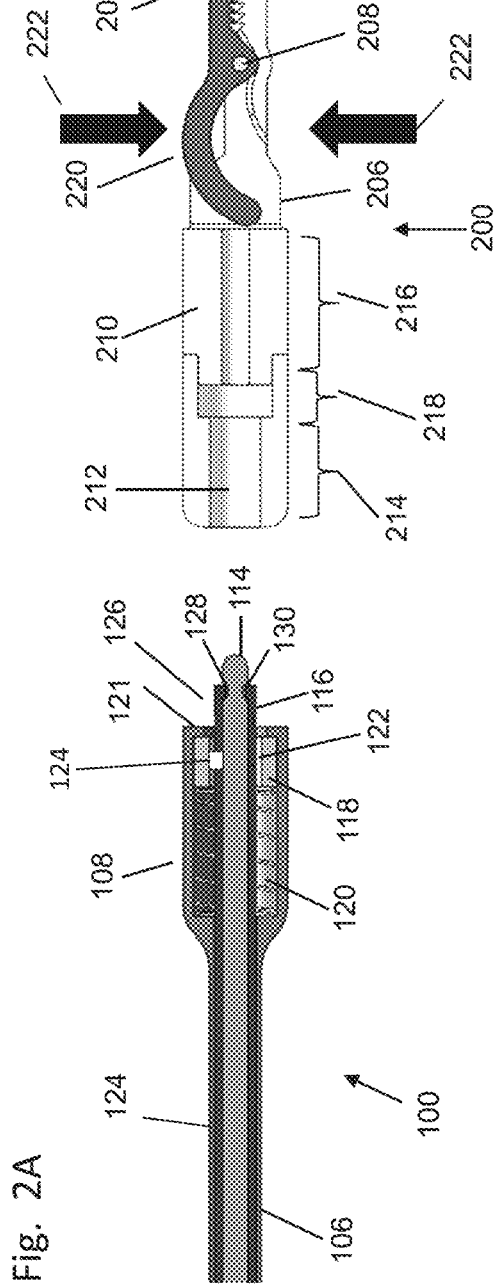

The delivery devices described here may be configured to actuate, couple to, and decouple from, the graspers described here in any suitable manner. For example, FIGS. 2A-2F illustrate one suitable mechanism by which a delivery device may be configured to actuate and couple/decouple a grasper. For example, FIG. 2A depicts a cross-sectional side view of variations of the grasper (200) and a distal portion of the delivery device (100) each described above with respect to FIGS. 1A-1C. As shown there, the grasper (200) may comprise a first jaw (202), a second jaw (204), and a main body (206). Generally, the first jaw (202) is rotatably connected to the main body (206) at a pivot point (208), such that the first jaw (202) may rotate relative to the main body (206). In some variations (such as that shown in FIGS. 2A-2F), the second jaw (204) may be fixed relative to the main body (206), while in other variations the second jaw (204) may also be rotatably connected to the main body (206). When the second jaw (204) is fixed relative to the main body, the second jaw (204) may be formed separately from the main body (206) and subsequently attached thereto, or may be formed integrally with the main body (206). When a jaw as described here is configured to rotate relative a pivot point, the jaw may be configured to rotate in any suitable manner. In some variations, a jaw may be connected to the main body via a rotation pin, such that the jaw may rotate around the rotation pin (or the jaw and rotation pin may rotate relative the main body). In other variations, the jaw may be connected to the main body via a living hinge.

The first jaw (202) and second jaw (204) may be rotationally biased toward each other (e.g., towards a closed configuration). In variations where the first jaw (202) is rotatably connected to the main body, the first jaw (202) may be rotationally biased toward the second jaw (204). For example, in some variations the grasper (200) may comprise a spring such as a torsional spring or a cantilever spring (not shown), which may spring-bias the first jaw (202) toward the second jaw (204). In variations where the second jaw (204) is rotatably connected to the main body, the second jaw (204) may also be biased towards the first jaw (202) (e.g., via one or more springs). The bias of the jaws toward the closed configuration may act to hold tissue positioned between the first jaw (202) and the second jaw (204).

As shown in FIG. 2A, the main body (206) of the grasper may comprise a barrel portion (210) with a lumen (212) extending therethrough. A portion of the delivery device (100) may be advanced through the lumen (212) to rotate first jaw (202) (and in some instances, the second jaw (204) in variations where the second jaw (204) is rotatably connected to the main body (206)) relative to the main body (206), as will be described in more detail below. In some variations, the lumen (212) may have a constant diameter. In other variations, different portions of the lumen (212) may have different diameters.

For example, in the variation of the grasper (200) shown in FIGS. 2A-2F, the lumen (212) of the barrel portion (210) may comprise a proximal segment (214), a distal segment (216), and an intermediate segment (218) positioned between the proximal segment (214) and the distal segment (216). As shown in FIG. 2A, the proximal segment (214) may have a larger diameter than the distal segment (216), and the intermediate segment (218) may have a larger diameter than both the proximal segment (214) and the distal segment (216). The proximal (214), distal (216), and intermediate (218) segments may aid in maintaining a coupling with the delivery device (100), as will be described in more detail below.

The barrel portion (210) of the grasper (200) may be sized and configured to be engaged by the distal engagement portion (108) of the delivery device (100) to releasably couple the grasper (200) to the delivery device (100). In some variations, the outer diameter of the barrel portion (210) may have a constant diameter, or may have different portions of the barrel portion (210) having different diameters, such as described in more detail below. Turning to the delivery device (100), in the variation of the delivery device shown in FIGS. 2A-2F, the delivery device (100) may comprise an actuation rod (114) slidably disposed in the shaft (106). The actuation rod (114) may be advanced through the lumen (212) of the barrel portion (210) of the grasper (200) to actuate the grasper (200), as will be described in more detail below. Also shown in FIG. 2A is a locking sheath (116), a coupling magnet (118), and a spring (120). Each of these components will be discussed further below.

While shown in FIGS. 2A-2F as having a coupling magnet (118), the delivery device (100) need not comprise a coupling magnet. In variations of the delivery device (100) that do comprise a coupling magnet (118), the coupling magnet (118) may be slidably housed in a housing of the distal engagement portion (108), and may be configured to releasably couple the delivery device (100) to the grasper (200). The coupling magnet (118) may be movable between an advanced position (as depicted in FIG. 2A) and a retracted position (as depicted in FIG. 2C). In variations where the delivery device comprises a spring (120), the spring (120) may be positioned in the distal engagement portion (108) to bias the coupling magnet (118) toward the advanced position.

Figure 2B:
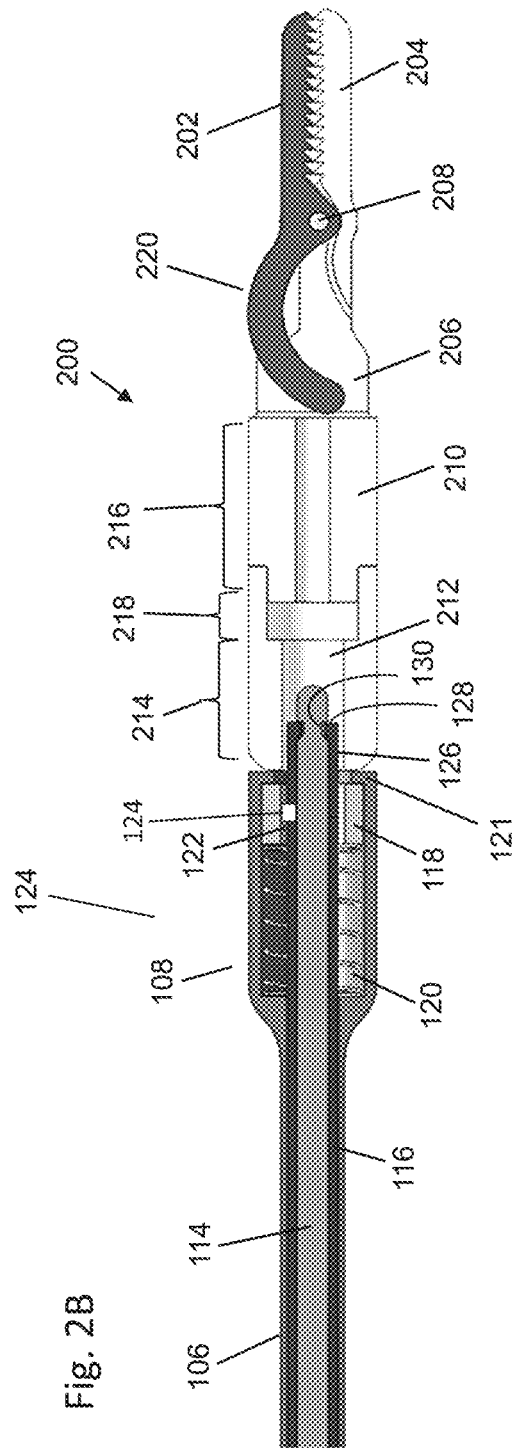

The delivery device (100) may be configured to couple to the grasper (200) when the coupling magnet (118) is in the advanced position. For example, when the distal engagement portion (108) is brought near the grasper (200), the coupling magnet (118) may attract the grasper (200). Generally, at least a portion of the graspers described here are formed from one or more metallic or magnetic materials which may be attracted to a magnetic field. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. Accordingly, one or more portions of the grasper (200) may be formed from or otherwise include a magnetic or ferromagnetic material, such that it may be attracted to a magnetic field produced by the coupling magnet (118). The attractive force provided by the coupling magnet (118) may hold the grasper (200) against or at least partially within the distal engagement portion (108), such as shown in FIG. 2B. The grasper (200) may be positioned such that a proximal end of the barrel portion (210) of the grasper is held against or at least partially within the distal engagement portion (108) of the delivery device (100).

To decouple the grasper (200) from the distal engagement portion (108), the coupling magnet (118) may be withdrawn to the retracted position, as shown in FIG. 2C. Because the force applied by a magnet decreases as a function of the distance from the magnet, moving the coupling magnet (118) to the retracted position may increase the distance between the grasper (200) and the coupling magnet (118) (e.g., the distal engagement portion (108) may comprise a stop (121) which may prevent the grasper from being retracted with the coupling magnet (118)), which may reduce the attractive force felt by the grasper (200). Eventually, the attractive force may be sufficiently diminished such that the grasper (200) may decouple from the delivery device (100).

The coupling magnet (118) may be retracted in any suitable manner. In some variations, the delivery device (100) may comprise a control sheath (not shown) which may be attached to the coupling magnet (118). The control sheath may be selectively withdrawn or advanced (e.g., via a control mechanism in the handle (104)) to withdraw and advance, respectively, the coupling magnet (118). In other variations, a portion of the actuation rod (114) may be configured to retract the coupling magnet (118). For example, the actuation rod (114) may be configured to catch on or otherwise engage the coupling magnet (118) during retraction of the actuation rod (114). In these variations, the actuation rod (114) may be withdrawn until the actuation rod (114) engages the coupling magnet (118). Once the actuation rod (114) engages the coupling magnet (118), further withdrawal of the actuation rod (114) may also withdraw the coupling magnet (118).

For example, as shown in FIGS. 2A-2F, the actuation rod (114) may be slidably disposed within a lumen (122) of the coupling magnet (118). In some variations, at least a segment of the actuation rod (114) may be sized and configured such that the portion of the actuation rod (114) cannot fully pass through the lumen (122). For example, in some variations a segment of the actuation rod may have a diameter greater than a diameter of the lumen (122). Additionally or alternatively, the segment may comprise one or more projections extending from an outer surface of the actuation rod (114) and which cannot fully pass through the lumen (122). When the segment of the actuation rod (114) is positioned distal to the coupling magnet (118), the actuation rod (114)

may be freely advanced relative to the coupling magnet (118). Conversely, withdrawal of the actuation rod (114) may pull the segment of the actuation rod (114) into contact with the coupling magnet (118). Since the segment cannot fully pass through the lumen (122) of the coupling magnet (118), further withdrawal of the actuation rod (114) may cause the segment of the actuation rod (114) to pull on and withdraw the coupling magnet (118). When the actuation rod (114) is subsequently advanced, the spring (120) may advance the coupling magnet (118) with the actuation rod (114) until the coupling magnet (118) reaches the advanced position.

In variations where the delivery device (100) comprises a locking sheath (116) slidably disposed in the lumen (122) of the coupling magnet (118), the locking sheath (116) may be configured to withdraw the coupling magnet (118). For example, a segment of the locking sheath (116) may be sized and configured such that the segment cannot fully pass through the lumen (122) of the coupling magnet (118), such as described above with respect to the actuation rod (114). In the variation shown in FIGS. 2A-2F, the locking sheath (116) may comprise a protrusion (124) positioned distally of the coupling magnet (118) and sized such that the protrusion (124) cannot fully pass through the lumen (122). In these variations, proximal withdrawal of the locking sheath (116) through the lumen (122) may place the protrusion (124) into contact with the coupling magnet (118), such as shown in FIGS. 2A and 2B. As depicted in FIG. 2C, further withdrawal of the locking sheath (116) may also withdraw the coupling magnet (118) (e.g., by virtue of the contact between the protrusion (124) and the coupling magnet (118)).

As mentioned above, the delivery devices described here may comprise a locking sheath (although it should be appreciated that in some variations the delivery device may not comprise a locking sheath). In variations where the delivery device does comprise a locking sheath (116), such as the variation of the delivery device (100) depicted in FIGS. 2A-2F, the locking sheath (116) may be slidably disposed in the shaft (106). The actuation rod (114) may in turn be positioned at least partially within the locking sheath (116). The locking sheath (116) may comprise an expandable distal portion (126) which may be configured to expand inside of the lumen (212) of the barrel portion (210) of the grasper (200) to temporarily engage an interior portion of the lumen (212), which may help maintain the coupling between the grasper (200) and the delivery device (100).

In these variations, the delivery device (100) may be configured such that advancement of the actuation rod (114) relative to the locking sheath (116) may expand the expandable distal portion (126) of the locking sheath (116). For example, the expandable distal portion (126) of the locking sheath (116) may comprise at least one internal projection (128) that projects inwardly and is sized and shaped to fit within at least one corresponding indentation (130) in the outer surface of the actuation rod (114). It should be appreciated that the at least one internal projection (128) may be a single projection (e.g., an annular snap-fit or a projection that extends radially around some or all of the inner circumference of the locking sheath (116)) or multiple discrete projections. Similarly, the actuation rod (114) may comprise a single indentation (e.g., an indentation that extends radially around some or all of the outer surface of actuation rod (114)) or multiple indentations.

The actuation rod (114) may be positioned within the locking sheath (116) such that the internal projections (128) of the locking sheath (116) are positioned in corresponding indentations (130) of the actuation rod (114), such as shown in FIGS. 2A-2D. This may create a friction fit or mechanical interlock between the actuation rod (114) and the locking sheath (116), which may cause the locking sheath (116) to be advanced and withdrawn with the actuation rod (114). The engagement between the actuation rod (114) and the locking sheath (116) may be further configured such that under certain circumstances the actuation rod (114) may be advanced relative to the locking sheath (116) to expand the expandable distal portion (126) of the locking sheath (116). For example, as shown in FIGS. 2A-2F, the internal projections (128) of the locking sheath (116) and the corresponding indentations (130) of the actuation rod (114) may each have a ramped proximal portion. When the internal projections (128) are positioned within corresponding indentations (130), the ramped proximal portion of each internal projection (128) may be positioned in contact with the ramped proximal portion of a corresponding indentation (130). This contact may provide the friction fit or mechanical interlock that may allow the actuation rod (114) to distally advance the locking sheath (116) as mentioned above.

When an external force is applied to the locking sheath (116) to resist distal advancement of the locking sheath (116), advancement of the actuation rod (114) may overcome the friction force or mechanical connection between the ramped proximal portions of the internal projections (128) and the corresponding indentations (130), at which point the contacting ramped surfaces may slide relative to each other as the actuation rod (114) begins to advance distally relative to the locking sheath (116). As the actuation rod (114) is advanced distally relative to the locking sheath (116), the internal projections (128) may slide out of their corresponding indentations (130) (such as shown in FIG. 2E), which may thereby expand the expandable distal portion (126) of the locking sheath (116).

Figure 2E:
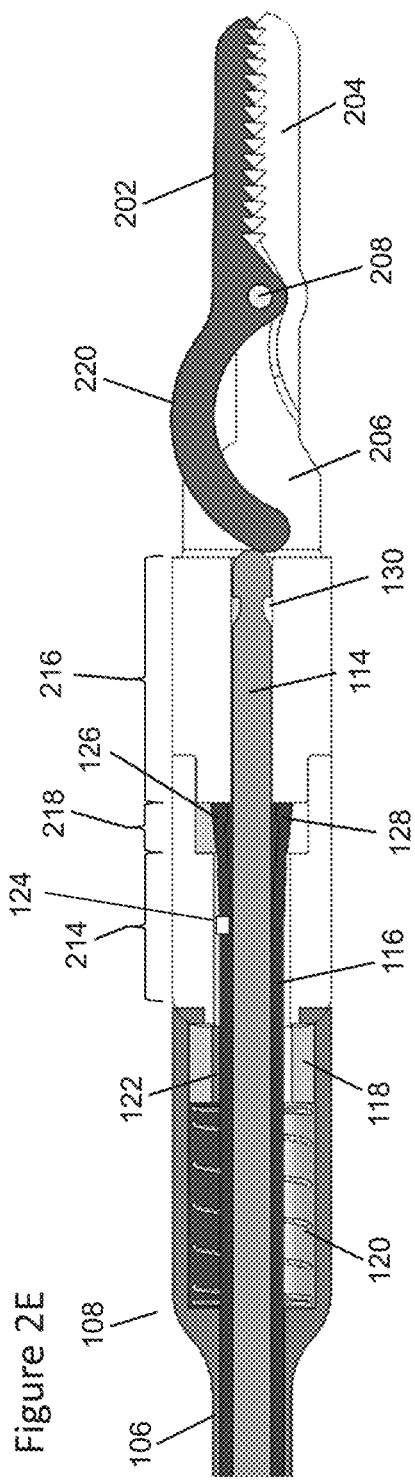
Figure 2F:
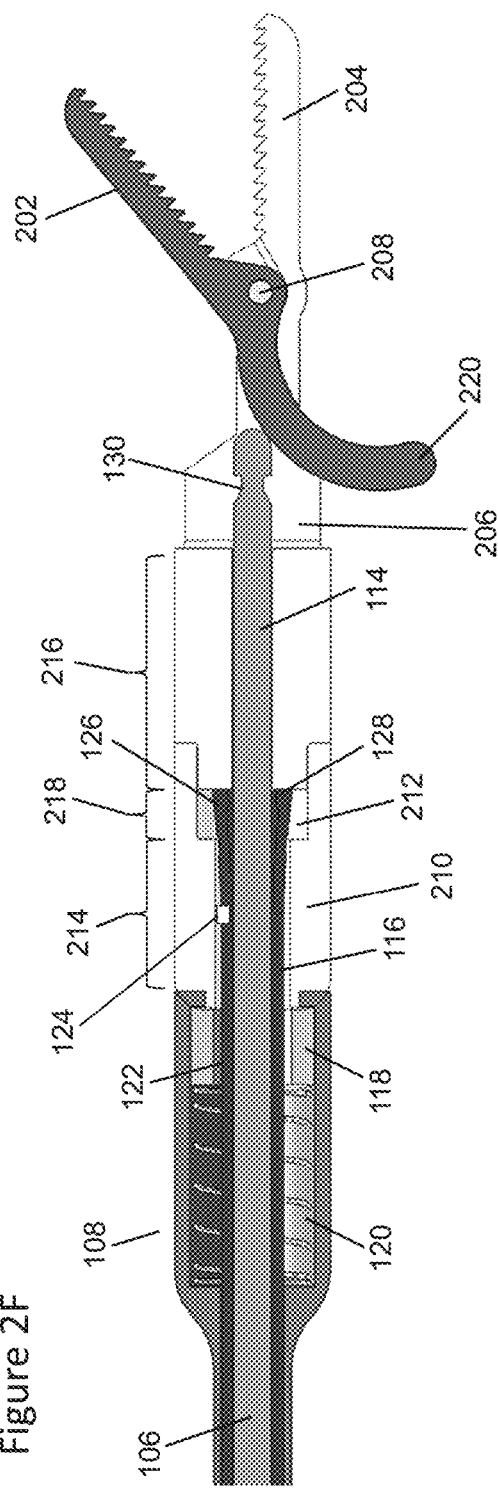

This expansion of the expandable distal portion (126) of the locking sheath (116) may help to maintain the temporary coupling between the delivery device (100) and the grasper (200), as illustrated in FIGS. 2D-2F. Specifically, the locking sheath (116) and actuation rod (114) may be positioned such that the internal projections (128) of the locking sheath (116) are positioned in respective indentations (130) on the actuation rod (114), which may allow advancement and retraction of the actuation rod (114) to advance and retract the locking sheath (116), as discussed above. The grasper (200) may be coupled to the distal engagement portion (108) of the delivery device (100), as shown in FIG. 2C, and the actuation rod (114) may be advanced to begin advancing the actuation rod (114) and locking sheath (116) into the lumen (212) of the barrel portion (210) of the grasper (200). The actuation rod (114) may be sized such that it is smaller than each of the proximal segment (214), the distal segment (216), and the intermediate segment (218) of the lumen (212) of the barrel portion (210) of the grasper (200). This may allow the actuation rod (114) to be advanced through the entire lumen (212) of the barrel portion. The locking sheath (116), however, may be sized and configured such that it may pass through the proximal segment (214) and the intermediate segment (218) of the lumen (212), but is prevented from entering the distal segment (216). Accordingly, the actuation rod (114) may be advanced to advance the actuation rod (114) and the locking sheath (116) through the lumen (212) of the barrel portion (210) of the grasper (200) until the locking sheath (116) reaches the distal segment (216) of the lumen (212), as shown in FIG. 2D. At this point, the locking sheath (116) may be prevented from entering the distal segment (216), and may thus be prevented from further advancement. The actuation rod (114) may be further advanced relative to the grasper (200) to advance the actuation rod (114) through the distal segment (216) of the lumen (212). Because the locking sheath (116) is prevented from advancing further, the actuation rod (114) may be advanced relative to the locking sheath (116). This may cause the internal projections (128) of the locking sheath (116) to slide out of their respective indentations (130) and expand the expandable distal portion (126) of the locking sheath (116), as depicted in FIG. 2E. Specifically, the expandable distal portion (126) may be positioned in the intermediate segment (118) of the lumen (112) when it is expanded.

When expanded, the expandable distal portion (126) may be configured to resist being removed from the lumen (212) of the barrel portion (210) of the grasper (200). Specifically, the expandable distal portion (126) of the locking sheath (116) may be sized and configured such that, when expanded, the expandable distal portion (126) may be prevented from passing through the proximal segment (214) of the lumen (212) (e.g., the outer diameter of the expanded distal portion (126) may be larger than the diameter of the proximal segment (214) of the lumen (212)). When the expandable distal portion (126) of the locking sheath (116) is expanded in the intermediate segment (218) (as shown in FIG. 2E), the locking sheath (116) may resist both advancement of the locking sheath (116) into the distal segment (216) (as discussed above) and withdrawal of the locking sheath (116) though the proximal segment (214) of the lumen (212). Accordingly, the expanded locking sheath (116) may lock the grasper (200) in place relative to the delivery device (100). When the actuation rod (114) is further advanced to actuate the jaws of the grasper (as shown in FIG. 2F, and discussed in more detail below), the actuation rod (114) may apply one or more forces to the grasper (200) which may have a tendency to push the grasper (200) away from the coupling magnet (118) (which in some instances could possibly inadvertently decouple the grasper (200) from the delivery device (100)), but the engagement between the expanded locking sheath (116) and the grasper (200) may overcome these forces to maintain the position of the grasper (200) relative to the delivery device (100).

To disengage the locking sheath (116) from the grasper (200), the actuation rod (114) may be retracted until the indentations (130) of the actuation rod (114) reach the internal projections (128) of the locking sheath (116). The expandable distal portion (126) of the locking sheath (116) may be biased toward an unexpanded state such that the internal projections (128) reposition themselves into their respective indentations (130), as shown in FIG. 2D. The actuation rod (114) may then be withdrawn to withdraw the locking sheath (116) (e.g., by virtue of the connection between the indentations (130) and the internal projections (128)).

The grasper (200) may be configured to be actuated in any suitable manner. In some variations, the grasper (200) may be configured such that it may be actuated by a force applied internally of the grasper (200) (e.g., via an actuation rod (114) of the delivery device (100) advanced through the lumen (212) of the barrel portion (210) of the grasper (200), as discussed in more detail below), and may be further configured such that it may be actuated by a force applied externally of a grasper (200) (e.g., via a grasping device). For example, in the variation of the grasper (200) shown in FIGS. 2A-2F, the grasper (200) may comprise a proximal arm (220) connected to the first jaw (202), wherein rotation of the proximal arm (220) rotates the first jaw (202) relative to the main body (206) and second jaw (204) of the grasper (200). The proximal arm (220) may act as a lever and/or a cam to rotate the first jaw (202).

For example, in some instances the proximal arm (220) may act as a cam to rotate the first jaw (202). In these instances, the actuation rod (114) of the delivery device (100) may rotate the first jaw (202). Specifically, a portion of the proximal arm (220) may be aligned relative to the lumen (212) such that advancement of the actuation rod (114) through the lumen (212) pushes the actuation rod (114) into contact with the proximal arm (220), as illustrated in FIG. 2E. Once in contact with the proximal arm (220), advancement of the actuation rod (114) may push against the proximal arm (220). The proximal arm (220) may act as a cam to convert the linear motion of the actuation rod (114) into rotation of the proximal arm (220), which may in turn rotate the first jaw (202) away from the second jaw (204) as shown in FIG. 2F. When the first jaw (202) is spring-biased toward the second jaw (204), the rotation of the proximal arm (220) may overcome this spring bias, which may allow the actuation rod (114) to hold the first jaw (202) in its open position. Additionally, the first jaw (202) may rotate back toward the second jaw (204) when the actuation rod (114) is retracted.

Additionally, in the variation of the grasper (200) shown in FIGS. 2A-2F, at least a portion of the proximal arm (220) may be exposed relative to the main body (206), which may allow a grasping device to grasp the proximal arm (220) to rotate the first jaw (202) relative to the second jaw (204). For example, opposing forces (represented by arrows (222) in FIG. 2A) may be applied (e.g., via a grasping device) to the exposed portion of the proximal arm (220) and the main body (206) to cause the proximal arm (220) to rotate around the pivot point (208) (which may in turn rotate the first jaw (202) away from the second jaw (204)).

Figure 3A:
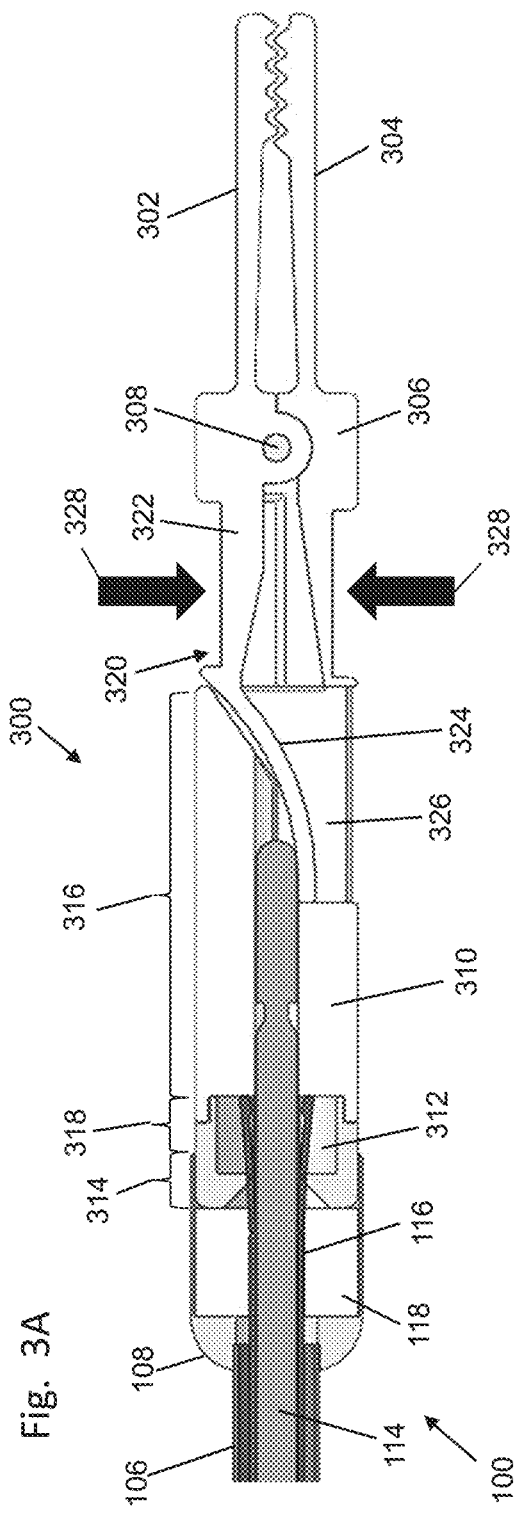
Figure 3B:
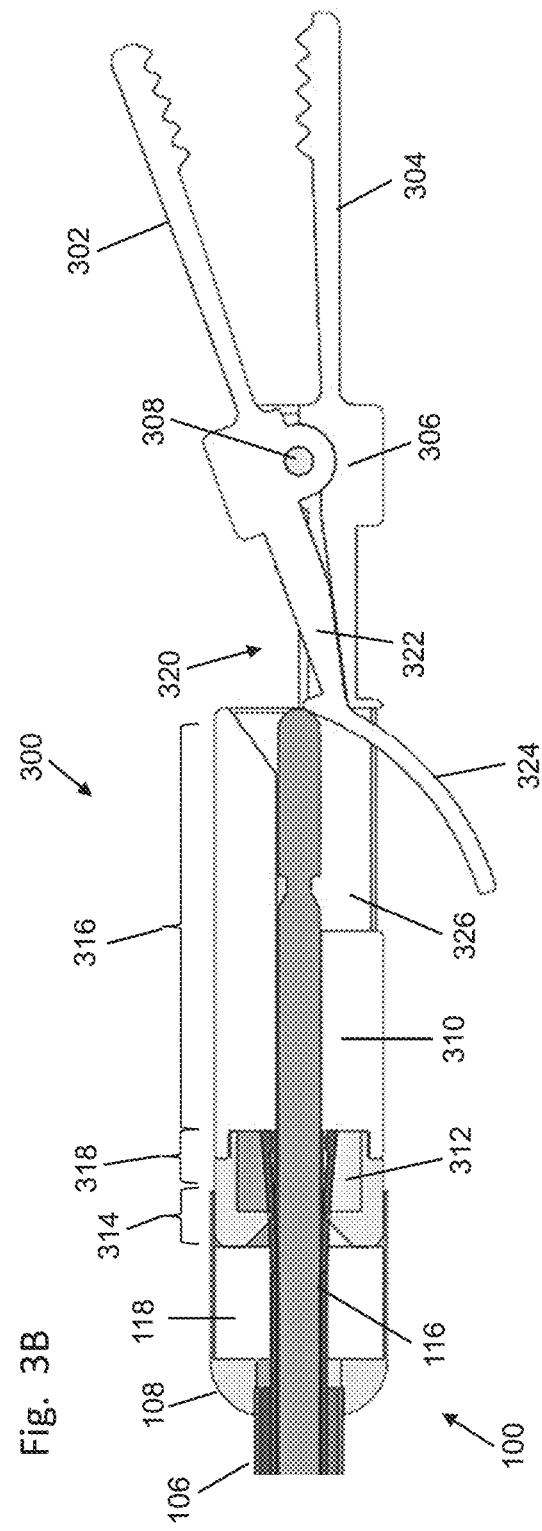

While the proximal arm (220) is shown in FIGS. 2A-2F as being curved, it should be appreciated that in some variations the graspers described here may comprise also comprise one or more straight segments. For example, FIGS. 3A and 3B depict cross-sectional side views of one such variation of a grasper (300) which may be used with the systems described here. As shown there, the grasper (300) may comprise a first jaw (302), a second jaw (304), and a main body (306). The first jaw (302) may be rotatably coupled to the main body (306) at a pivot point (308), and the main body (306) of the grasper (300) may comprise a barrel portion (310) having a lumen (312) extending therethrough. In some variations, the lumen (312) may comprise a proximal segment (314), a distal segment (316), and an intermediate segment (318), which may be configured as described above with respect to the variation of the grasper (200) depicted in FIGS. 2A-2F.

As shown in FIGS. 3A and 3B, the grasper (300) may comprise a proximal arm (320) connected to or otherwise extending from the first jaw (302) such that rotation of the proximal arm (320) around the pivot point (308) also rotates the first jaw (302) around the pivot point. In this variation, the proximal arm (320) may comprise a straight segment (322) and a curved segment (324), and the proximal arm (320) may act as a cam and/or lever to rotate the first jaw (302). Specifically, the straight segment (322) may be positioned between the curved segment (324) and the first jaw (302), and may provide a flat surface which may facilitate engagement of the proximal arm (320) by a grasping device. For example, as shown in FIGS. 3A and 3B, at least a portion of the straight segment (322) may be exposed from the main body (306). Some or all of the curved segment (324) may also be exposed, although in some variations, the curved segment (324) may be at least partially positioned within a channel (326) in the barrel portion (310) of the grasper (300). Opposing forces (represented in FIG. 3A by arrows (328)) may be applied (e.g., via a grasping device) to an exposed portion of the straight segment (322) (and/or an exposed portion of the curved segment (324), when at least a portion of the curved segment (324) is exposed) and the main body (306), which may cause the proximal arm (320) to act as a lever to rotate around the pivot point (308). This in turn may rotate the first jaw (302) away from the second jaw (304), as illustrated in FIG. 3B. When the first jaw (302) is configured to be rotatably biased toward the second jaw (304) (e.g., via one or more springs, as described in more detail above), and the forces (328) holding the first jaw (302) rotated away from the second jaw (304) are removed from the proximal arm (320) and the main body (306), the first jaw (302) may rotate back toward the second jaw (304), as illustrated in FIG. 3A. When tissue is positioned between the first jaw (302) and the second jaw (304), this may connect the grasper (300) to the tissue as discussed in more detail above.

Additionally, a delivery device (such as the delivery device (100) described above with respect to FIGS. 1A-1C and 2A-2F) may be configured to actuate the jaws of the grasper (300) through the barrel portion (310), as illustrated in FIGS. 3A and 3B. The distal engagement portion (108) of the delivery device (100) may engage the barrel portion (310) of the grasper (300) (as discussed in more detail above), and the actuation rod (114) may be advanced through the lumen (312) of the barrel portion (310) until the actuation rod (114) contacts the curved segment (324) of the proximal arm (320), such as shown in FIG. 3A. In some instances, advancing the actuation rod (114) to this point may cause a locking sheath (116) of the delivery device (100) to couple to the lumen (312) of the barrel portion (310) of the grasper (300), such as described in more detail above. Further advancement of the actuation rod (114) may push the actuation rod (114) against the curved segment (324) of the proximal arm (320), and the proximal arm (320) may act as a cam to convert the linear movement of the actuation rod (114) into rotational movement of the proximal arm (320). As the actuation rod (114) rotates the proximal arm (320), the first jaw (302) may rotate away from the second jaw (304), as depicted in FIG. 3B. When the actuation rod (114) is withdrawn, the first jaw (302) may be biased to rotate toward the second jaw (304) to return the first jaw (302) toward the second jaw (304). Accordingly, the actuation rod (114) may be advanced and withdrawn to cause the first jaw (302) to rotate away from and toward, respectively, the second jaw (304). Additionally, positioning the straight segment (322) between the curved segment (324) and the pivot point (308) may create a longer moment arm, which may reduce the force that must be applied to the curved segment (324) by the actuation rod (104) in order to rotate the first jaw (302). While the proximal arm (320) shown in FIGS. 3A and 3B is configured such that a concave portion of the curved segment (324) faces the lumen (312) such that the actuation rod (114) contacts the concave portion of the curved segment (324) during advancement of the actuation rod (114), the curved segment may instead be configured such that a convex portion of a curved segment faces the lumen such that the actuation rod (114) contacts the convex portion of the curved segment during advancement of the actuation rod (114).

While the variations of the graspers depicted in FIGS. 2A-2F and 3A-3B each comprise a proximal arm that is configured to be used as both a cam and a lever to actuate the grasper, in some variations the grasper may comprise a first mechanism which may act as a cam to actuate the grasper and a second mechanism which may act as a lever to actuate the grasper. For example, FIGS. 4A and 4B depict one such variation of a grasper (400) suitable for use with the systems described here. As shown there, the grasper (400) may comprise a first jaw (402), a second jaw (404), and a main body (406). The first jaw (402) may be rotatably coupled to the main body (406) at a pivot point (408), and the main body (406) of the grasper (400) may comprise a barrel portion (410) having a lumen (412) extending therethrough. In some variations, the lumen (412) may comprise a proximal segment (414), a distal segment (416), and an intermediate portion (418), which may be configured as described above with respect to the variation of the grasper (200) depicted in FIGS. 2A-2F.

Also shown in FIGS. 4A and 4B are a proximal arm (420) and an eccentric cam member (422). Each of the proximal arm (420) and the eccentric cam member (422) may be attached to the first jaw (402), such that rotation of either the proximal arm (420) or the eccentric cam member (422) relative to the pivot point (408) may rotate the first jaw (402). For example, opposing forces (represented by arrows (428)) may be applied to the main body (406) and the proximal arm (420), which may rotate the proximal arm (420) relative to the main body (406) and act as a lever to rotate the first jaw (402) away from the second jaw (404), such as shown in FIG. 4B. In some variations, the first jaw (402) may be rotatably biased toward the second jaw (404) (e.g., via one or more springs, as described in more detail above), such that when the forces (428) are removed from the proximal arm (420) and/or main body (406), the first jaw (402) may rotate back toward the second jaw (404), as illustrated in FIG. 4A.

Similarly, the eccentric cam member (422) may be rotated via a portion of a delivery device that may be advanced through the lumen (412) of the barrel portion (410) of the grasper (400). In some instances, the delivery device (100) described above may actuate the grasper (400). The distal engagement portion (108) of the delivery device (100) may engage the barrel portion (410) of the grasper (400) (as discussed in more detail above), and the actuation rod (114) may be advanced through the lumen (412) of the barrel portion (410) until the actuation rod (114) contacts the eccentric cam member (422) (which may be aligned with the lumen (412)), such as shown in FIG. 4A. In some instances, advancing the actuation rod (114) to this point may cause a locking sheath (116) of the delivery device (100) to couple to the lumen (412) of the barrel portion (410) of the grasper (400), such as described in more detail above. Further advancement of the actuation rod (114) may push against the eccentric cam member (422), which may convert the linear movement of the actuation rod (114) into rotational movement of the eccentric cam member (422). As the actuation rod (114) rotates the eccentric cam member (422), the first jaw (402) may rotate away from the second jaw (404), as depicted in FIG. 4B. When the actuation rod (114) is withdrawn, the first jaw (402) may be biased to rotate back toward the second jaw (404). Accordingly, the actuation rod (114) may be advanced and withdrawn to cause the first jaw (402) to rotate away from and toward, respectively, the second jaw (404).

Returning to FIGS. 2E-2F, the actuation rod (114) may be advanced and withdrawn in any suitable manner. For example, when the delivery device (100) comprises an actuation control mechanism, such as a slider, knob, trigger, or the like, the actuation control mechanism may be operatively connected to the actuation rod (114) such that the actuation control mechanism may advance and withdraw the actuation rod (114). For example, in the variation of the delivery device (100) shown in FIGS. 1A-1C, the trigger (112) may be configured to advance and retract the actuation rod (114). In some of these variations, the trigger (112) may be configured such that rotation of the trigger (112) toward the grip portion (110) withdraws the actuation rod (114) relative to the shaft (106), while rotation of the trigger away from the grip portion (110) advances the actuation rod (105) relative to the shaft. In these variations, when the trigger (112) is in the first position (as shown in FIG. 1A), the actuation rod (114) may be positioned as shown in FIGS. 2A and 2B with the coupling magnet (118) in an advanced position, which may allow the distal engagement portion (108) to connect to a grasper (such as grasper (200), as illustrated in FIGS. 1A and 2B). The trigger (112) may be rotated toward the grip portion (110) to position the trigger (112) in the third position (as shown in FIG. 1C), and this rotation may retract the actuation rod (114) relative to the shaft (106). Retraction of the actuation rod (114) may also withdraw the coupling magnet (118) to a retracted position, such as illustrated in FIG. 2C, which may decouple a grasper from the delivery device (100) as described above. The trigger (112) may be rotated away from the grip portion (110) and back to the first position to advance the actuation rod (114) back to the position shown in FIGS. 2A and 2B. Further rotation of the trigger (112) away from the grip portion (110) may move the trigger (112) from the first position to the second position (as shown in FIG. 1B) and may advance the actuation rod (114) through a lumen of a barrel portion of a grasper (e.g., the lumen (212) of the barrel portion (210) of the grasper (200) described above) to rotate one or more jaws of the grasper (as shown in FIG. 2F). Returning the trigger (112) to the first position (e.g., by rotating the trigger (112) toward the grip portion (110)) may withdraw the actuation rod (114) relative to the shaft (106) and the grasper, which may allow the grasper to return to a closed configuration. It should be appreciated that in some variations, rotation of the trigger (112) toward the grip portion (110) may be configured to advance the actuation rod (114) relative to the shaft (106), while rotation of the trigger (112) away from the grip portion (110) may retract the actuation rod (114) relative to the shaft (106).

Figure 6A:
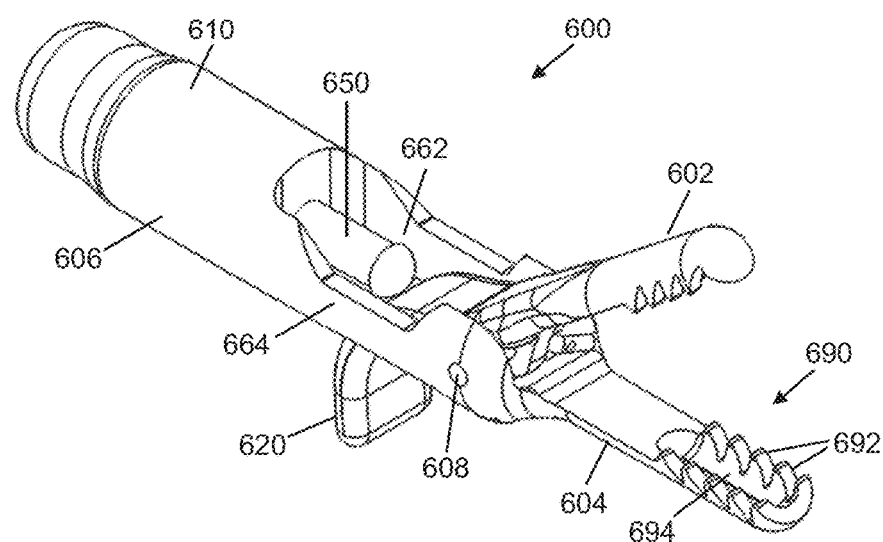
FIGS. 6A and 6B show perspective and side views, respectively, of a variation of a grasper as described here.
Figure 6B:
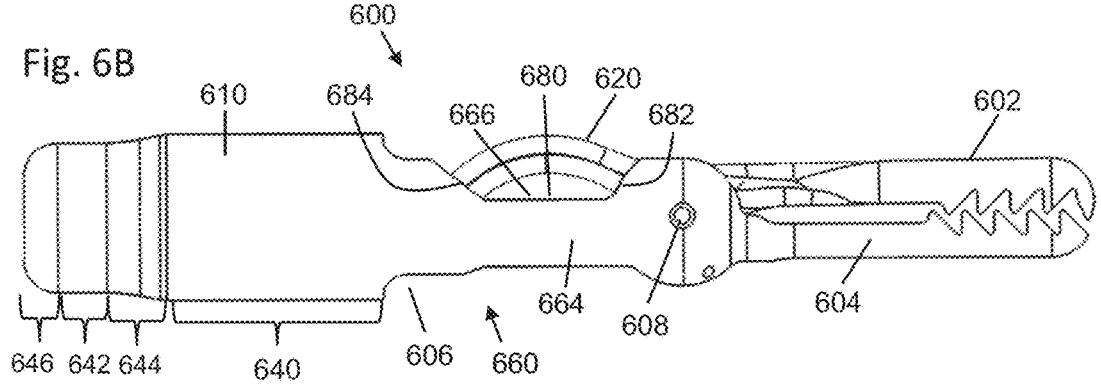
Figure 6C:
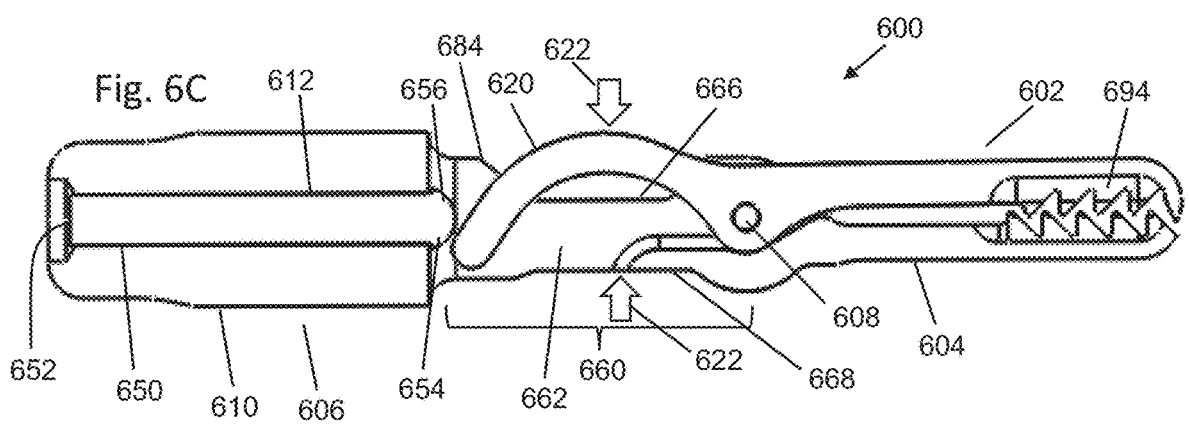
FIG. 6C shows a cross-sectional side view of the grasper of FIGS. 6A and 6B.

FIGS. 6A-6C depict another variation of a grasper (600) as described here. Specifically, FIGS. 6A and 6B show perspective and side views, respectively, of the grasper (600). As shown there, the grasper (600) may comprise a first jaw (602), a second jaw (604), and a main body (606). Generally, the first jaw (602) may be rotatably connected to the main body (606) at a pivot point (608), such that the first jaw (602) may rotate relative to the main body (606). While the second jaw (604) is shown in FIGS. 6A-6C as being fixed relative to the main body (606), it should be appreciated that in some variations the second jaw (604) may be rotatably connected to the main body (606), such as discussed in more detail above. The first jaw (602) (and/or the second jaw (604) in variations where the second jaw (604) is rotatably connected to the main body (606)) may be rotated relative to the main body (606) to actuate the grasper (600) between an open configuration and a closed configuration. Specifically, in the open configuration, the first jaw (602) and the second jaw (604) may be held in rotationally separated positions to define a space between the first jaw (602) and the second jaw (604), as shown in FIG. 6A. In the closed configuration, the first jaw (602) and second jaw (604) may be rotationally biased toward each other, as shown in FIG. 6B. While the first jaw (602) is shown as contacting the second jaw (604) in FIG. 6B, it should be appreciated that when the grasper (600) is connected to tissue, tissue positioned between the first jaw (602) and the second jaw (604) may prevent the first jaw (602) from contacting the second jaw (604) when the grasper is in the closed configuration. The first jaw (602) and second jaw (604) may be rotationally biased toward a closed configuration in any suitable manner (e.g., via a torsional spring (not shown)), such as described in more detail above.

The main body (606) of the grasper (600) may comprise a barrel portion (610) with a lumen (612) extending therethrough. A portion of a delivery device may be advanced at least partially into the lumen (612) to actuate the grasper (600) between closed and an open configurations, as will be discussed in more detail below. The outer diameter of the barrel portion (610) may be uniform, or may vary along the length of the barrel portion (610). For example, in the variation of the grasper (600) shown in FIGS. 6A-6C, the barrel portion (610) may have a first segment (640) having a first outer diameter and a second segment (642) having a second outer diameter. In some variations, the second outer diameter may be greater than the first outer diameter, which may allow the second segment (642) to act as a stop when engaged by a delivery device, such as will be discussed in more detail above. For example, in some variations the first segment may have a first outer diameter of about 10 mm, and the second segment may have an outer diameter between about 7 mm and about 9 mm.

In some variations (such as the variation of grasper (600) illustrated in FIGS. 6A-6C), the barrel portion (610) may further comprise a tapered portion (644) positioned between the first segment (640) and the second segment (642), such that the outer diameter of the tapered segment (644) tapers between the first outer diameter and the second outer diameter. It should be appreciated, however, that the barrel portion (610) need not have such a tapered portion (644), and the first segment (640) may immediately transition to the second segment (642). In variations that do include a tapered segment (644), the tapered segment (644) may provide a gradual diameter transition between the first (640) and second (642) segments, which may in turn reduce the presence of edges that may catch on or otherwise disturb tissue during use of the grasper (600).

Additionally or alternatively, the barrel portion (610) may have a tapered segment (646) at a proximal end of the barrel portion (610), which may also be at a proximal end of the first segment (640). In these variations, the diameter of the tapered segment (646) may taper from the first outer diameter of the first segment (640) to a third outer diameter smaller than that of the first outer diameter. In variations that include a tapered segment (646) at a proximal end of the barrel portion (610), the tapered diameter may facilitate alignment of the barrel portion (610) with a portion of the delivery device. Specifically, when a proximal end of the barrel portion (610) is inserted into a portion of a delivery device (as described in more detail below), the tapered segment (646) may help guide the barrel portion (610) into the delivery device, which may be beneficial in instances where the delivery device (or another retrieval device) is connected to the grasper to retrieve the grasper.

The first jaw (602) may be configured to rotate in any suitable manner such as described above. For example, in the variation of the grasper (600) shown in FIGS. 6A-6C, the grasper (600) may comprise a proximal arm (620) connected to the first jaw (602) such that rotation of the proximal arm (620) relative to the pivot point (608) rotates the first jaw (602) relative to the pivot point (608) (which may also rotate the first jaw (602) relative to the main body (606) and/or the second jaw (604)). While the proximal arm (620) shown in FIGS. 6A-6C may comprise a curved arm (620) that may be configured to act as both a cam and a lever (similar to the proximal arm (220) of the grasper (200) discussed above with respect to FIGS. 1A-1C and 2A-2F), it should be appreciated that the grasper may include any of the proximal arms and/or eccentric cam members discussed above with respect to FIGS. 3A-3B and 4A-4B. The proximal arm (620) (and/or an eccentric cam member) may assist in actuation of the grasper (600), as described hereinthroughout.

Generally, at least a portion of the proximal arm (620) may be exposed relative to the main body (606), which may allow a grasping device to grasp the proximal arm (620) to rotate the first jaw (602) relative to the second jaw (604), as will be discussed in more detail below. Specifically, the main body (606) may comprise a barrel extension (660) between the barrel portion (610) and the pivot point (608). As shown in a cross-sectional side view in FIG. 6C, the barrel extension (660) may comprise a channel (662) extending at least partially through the barrel extension (660). In the variation shown in FIGS. 6A-6C, the channel (662) may extend entirely through the barrel extension (660). The barrel extension (660) may have a wall (664) on one or both sides of the channel (662). In the variation shown in FIGS. 6A-6C, the barrel extension (660) may have a wall (664) on each side of the channel (662). The proximal arm (620) may be positioned at least partially within the channel (662), and may be configured to rotate through the channel (662) as the grasper (600) is actuated between open and closed configurations.

Generally, each wall (664) of the barrel extension (660) may have a top edge (666) and a bottom edge (668). The top edge (666) and bottom edge (668) may have any suitable profile, and together may define a height of the wall (664). For example, in the variation shown in FIGS. 6A-6C, the bottom edge (668) may be linear and substantially parallel to a longitudinal axis, while the top edge (666) may include a linear portion (680) positioned between two ramped segments (labeled (682) and (684)). In these variations, the height of the walls (664) may decrease along each of the ramped segments (682) and (684) toward the linear portion (680). This may facilitate grasping of the grasper (600) with a grasping device, as will be described in more detail below. In other variations, the top edge (666) and/or the bottom edge (668) may have a curved profile.

In some variations, the graspers described here may comprise a shuttle pin at least partially positioned in a lumen of the barrel portion of the grasper. Generally, the shuttle pin may reduce the distance an actuation rod may need to be inserted into the barrel portion in order to actuate the grasper. For example, in the variation of the grasper (600) shown in FIG. 6C, the grasper (600) may further comprise a shuttle pin (650). The shuttle pin (650) may be positioned at least partially within the lumen (612) of the barrel portion (610) of the grasper (600) and may be configured to slide relative to the lumen (612). The shuttle pin (650) may have a proximal end (652) and a distal end (654), and may assist in actuation of the grasper (600). Specifically, advancement of a portion of a delivery device (e.g., an actuation rod) into the lumen (612) of the barrel portion (610) may cause the delivery device to contact the proximal end (652) of the shuttle pin (650) and advance the shuttle pin (650) relative to the lumen (612). As the shuttle pin (650) is advanced relative to the lumen (612) of the barrel portion (610), the distal end (654) of the shuttle pin (650) may press against the proximal arm (620) (or an eccentric cam member, in variations where the grasper includes an eccentric cam member), which may cause the proximal arm (620) to act as a cam member, such as discussed in more detail above. Without the shuttle pin (650), an actuation rod may otherwise need to be inserted into the barrel portion (610) until it contacts the proximal arm (620) directly, such as discussed above. When the delivery device is withdrawn relative to the shuttle pin (650), the return bias of the first jaw (202) toward a closed configuration may push the shuttle pin (650) proximally relative to the lumen (612) of the barrel portion (610). While the variations of the graspers discussed above with respect to FIGS. 2A-2F, 3A, 3B, 4A, and 4B are not depicted as having a shuttle pin, it should be appreciated that any of these graspers may comprise a shuttle pin, which may be configured in any suitable manner as discussed with respect to shuttle pin (650) of the grasper (600) shown in FIGS. 6A-6C.

In variations where the graspers described here comprise a shuttle pin, the grasper may be configured to help prevent the shuttle pin from disengaging from the grasper. In some variations, at least a portion of a shuttle pin may be configured to have an outer profile that is larger than at least a portion of the lumen of the barrel portion of a main body. For example, in the variation of the shuttle pin (650) shown in FIG. 6C, the distal end (654) may comprise a cap (656) that may have an outer diameter sized to be larger than the lumen (612) of the barrel portion (610) of the main body (606). The shuttle pin (650) may be positioned in the lumen (612) such that the cap (656) is positioned distally of the lumen (612). Because the cap (656) is sized larger than the lumen (612), it may be prevented from entering the lumen (612) as the shuttle pin (650) is slid proximally relative to the barrel portion (610). Accordingly, the shuttle pin (650) may slide proximally until the cap (656) contacts the barrel portion (610), at which point the cap (656) may act as a stop to prevent further proximal movement of the shuttle pin (650). This may prevent the shuttle pin (650) from sliding out of the proximal end of the barrel portion (610) and disengaging the grasper (600).

Additionally, the grasper (600) may be configured to limit the amount of distal advancement of the shuttle pin (650). Generally, a portion of a proximal arm or an eccentric cam member (e.g., the proximal arm (620) of grasper (600)) may be aligned with the lumen of the barrel portion, which may resist or stop forward advancement of the shuttle pin (650) due to gravitational forces. When a delivery device or other device is used to advance the shuttle pin (650) to rotate the proximal arm and/or eccentric cam member, the delivery device and/or grasper may be configured to limit advancement of the shuttle pin (e.g., by blocking advancement of the shuttle pin (650) when the grasper is opened, as discussed in more detail below). In some of these variations, when a delivery device is used to advance the shuttle pin (650), it may be configured to advance the shuttle pin a predetermined distance (e.g., about 1 cm, about 1.25 cm, about 2 cm, or the like)) to actuate the grasper (600). In these variations, the shuttle pin (650) may be sized to be longer than this predetermined distance (e.g., greater than about 2.5 cm, greater than about 3 cm, or the like), such that a least a portion of the shuttle pin (650) may remain in the lumen when fully advanced by the delivery device. In some of these variations, the shuttle pin may be sized with a length such that at least a predetermined length (e.g., about 1.25 cm) of the shuttle pin remains in the lumen (612) when the shuttle pin (650) has been advanced the predetermined distance (e.g., for an advancement distance of about 1.25 cm, the shuttle pin may have a length of about 2.5 cm). Additionally or alternatively, the grasper (600) may be configured to limit the amount that the delivery device may advance the shuttle pin (650). For example, in some variations, a portion of the grasper (600) may be positioned in the path of the shuttle pin (650) and resists further advancement of the shuttle pin (650) by the delivery device. For example, the pivot point (608) may be positioned along the movement path of the shuttle pin (650). In these variations, the distal end (654) of the shuttle pin (650) may be stopped from further advancement by a portion of the first jaw (602) and/or the proximal arm (620) (and/or the eccentric cam member, in variations where the grasper contains an eccentric cam member) near the pivot point (608).

The grasper (600) shown in FIGS. 6A-6C may be actuated in any suitable manner. In some variations, the grasper (600) may be configured such that it may be actuated by a force applied internally of the grasper (600) (e.g., via an actuation rod of a delivery device advanced through the lumen (612) of the barrel portion (610) of the grasper (600), as discussed in more detail below), and may be further configured such that it may be actuated by a force applied externally of a grasper (600) (e.g., via a grasping device). FIGS. 7A-7D depict cross-sectional side views of a distal portion of a delivery device (700) and a manner of actuating the grasper (600) using the delivery device (700). The delivery device (700) and grasper (600) may be configured for laparoscopic introduction into the body, such as described above. Specifically, the delivery device (700) may comprise a handle (not shown), a shaft (706) extending from the handle, and a distal engagement portion (708) at a distal end of the shaft (706). The handle may comprise an actuation control mechanism that may be manipulated by a user to controllably actuate the grasper, and may be configured as described above with respect to the handle (104) of the delivery device (100) described above with respect to FIGS. 1A-1C. In some of these variations, the actuation control mechanism may comprise a trigger.

In some of these variations, the actuation control mechanism may be configured to both actuate the grasper (600) and the delivery device (700). In variations where the actuation control mechanism comprises a trigger, the trigger may be moveable between three positions (although it should be appreciated that the trigger may assume one or more intermediate positions between these positions). Of the three positions, the trigger may be moveable between a first position (such as the position of the trigger (112) of the delivery device (100) shown in FIG. 1A) and a second position (such as the position of the trigger (112) of the delivery device (100) as shown in FIG. 1B) to close and open, respectively, the grasper (600). The trigger may be moveable to a third position (such as the position of the trigger (112) of the delivery device (100) as shown in FIG. 1C) to eject or otherwise release the grasper (600) from the delivery device (700). In some of these variations, to move the trigger from the second position (in which the grasper (600) is placed in an open configuration) to the third position (to eject the grasper (600) from the delivery device (700)), the trigger may need to be moved through the first position, thereby moving the grasper (600) to a closed configuration prior to ejecting the grasper (600).

Figure 7A:
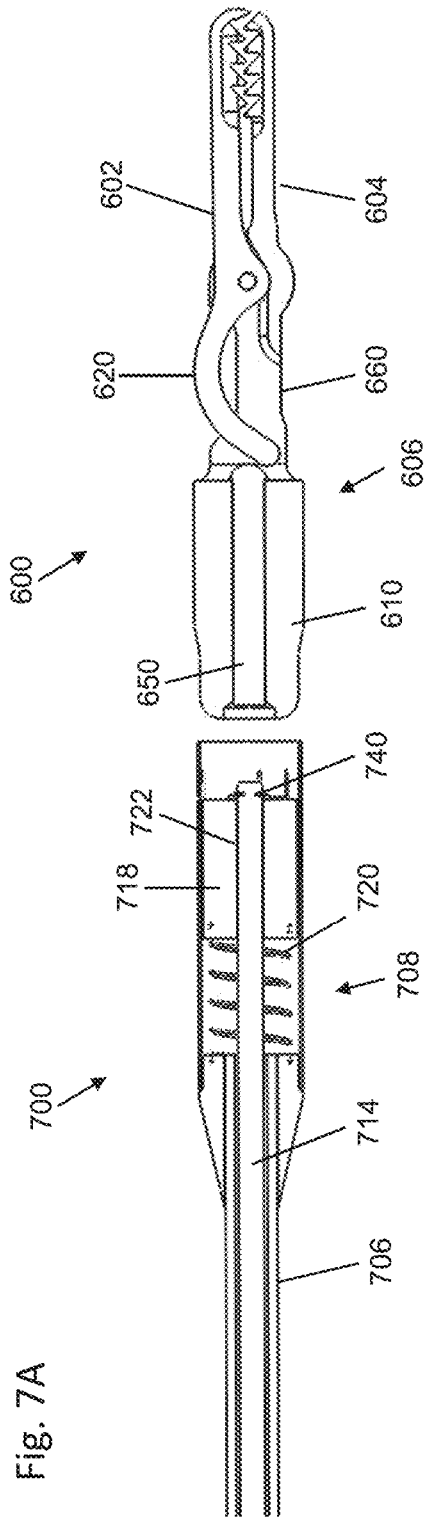
FIGS. 7A-7D depict cross-sectional side views of a distal portion of a variation of the delivery devices described here and the grasper of FIGS. 6A and 6B.
Figure 7B:
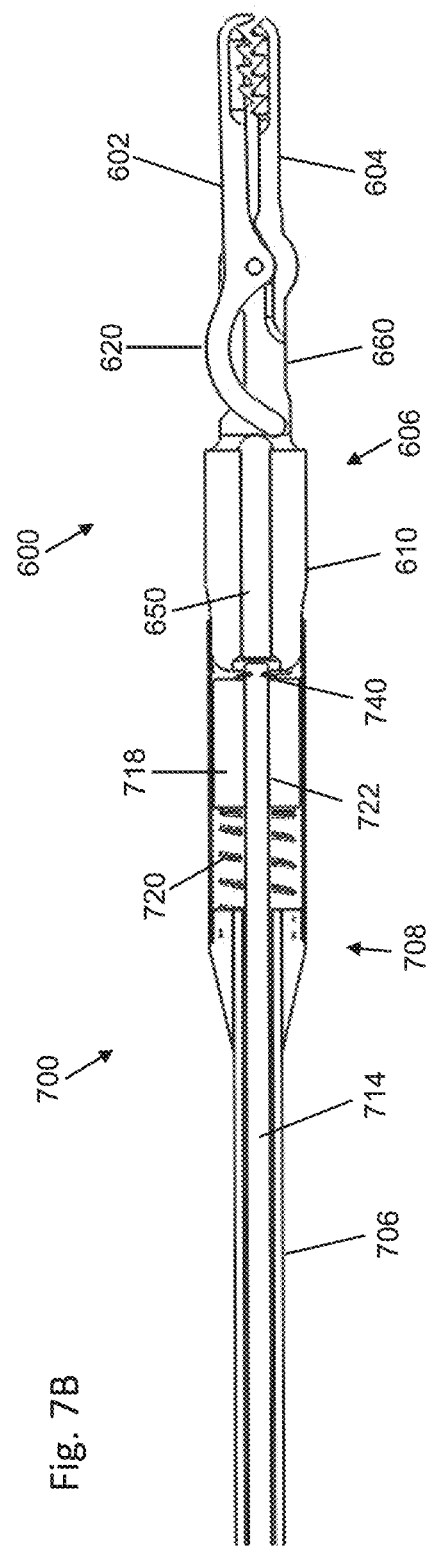
Figure 7C:
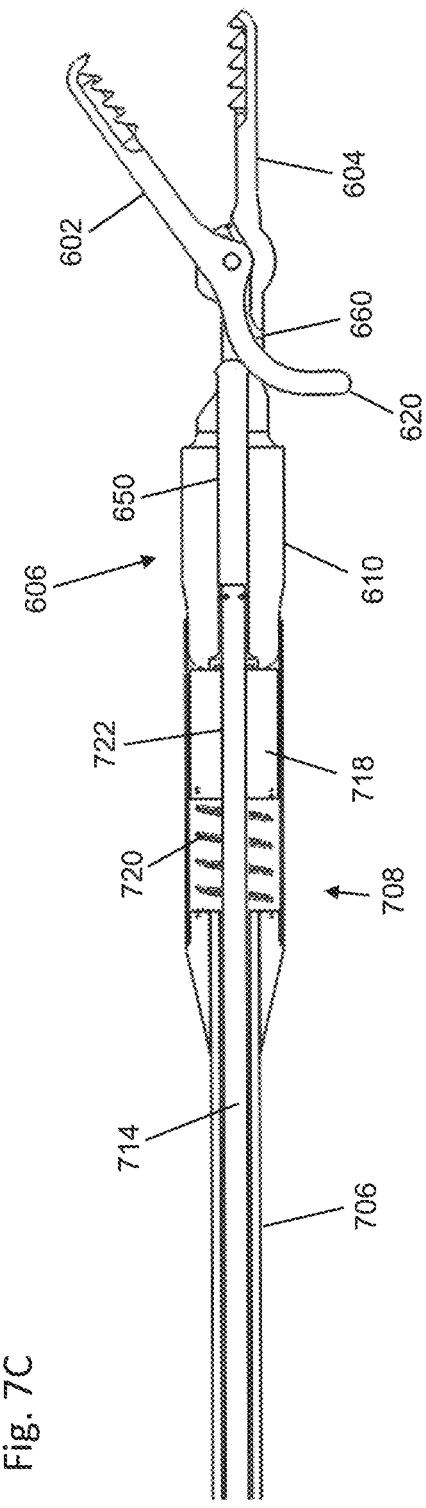
Figure 7D:
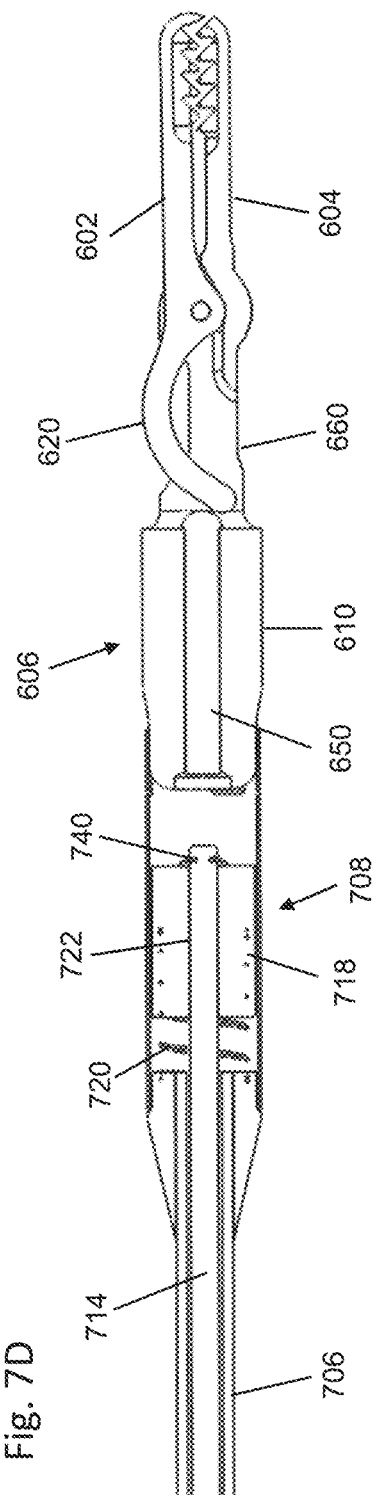

Returning to FIGS. 7A-7D, in some variations the distal engagement portion (708) of the delivery device (700) may comprise a coupling magnet (718) and a spring (720). In these variations, the coupling magnet (718) may be slidably housed in the distal engagement portion (708) (e.g., in a housing of the distal engagement portion (708)). The coupling magnet (718) may be moveable between an advanced position (as depicted in FIGS. 7A-7C) and a retracted position (as depicted in FIG. 7D). The spring (720) may be positioned within the distal engagement portion (708) such that the spring (720) biases the coupling magnet (718) toward the advanced position. The delivery device (700) may be configured to couple to the grasper (600) when the coupling magnet (718) is in the advanced position. As mentioned above, at least a portion of the grasper (600) may be formed from one or more metallic or magnetic materials. When the grasper (600) is positioned near the distal engagement portion (708) (such as shown in FIG. 7A), the coupling magnet (718) attract the grasper (600) and temporarily couple the grasper (600) to the delivery device (700).

Specifically, when the grasper (600) is temporarily coupled to the delivery device (700), at least a portion of the barrel portion (610) may be positioned within the distal engagement portion (708), as shown in FIG. 7B. The attractive force between the coupling magnet (718) and the grasper (600) may hold the grasper (600) in place. In variations where the grasper (600) has a barrel portion (610) having a first segment (640) having a first outer diameter and a second segment (642) having a second outer diameter, the first outer diameter may be sized to fit within the distal engagement portion (708) while the second outer diameter may be sized such that it is too large to fit within the distal engagement portion (708). In these variations, the second segment (642) (or a tapered segment (644) between the first segment (640) and the second segment (642)) may act as a stop to limit the amount of the barrel portion (610) that may enter the distal engagement portion (708).

To decouple the grasper (600) from the distal engagement portion (708), the coupling magnet (718) may be withdrawn to the retracted position, such as shown in FIG. 7D. As the coupling magnet (718) is retracted, the attractive force between the coupling magnet (718) and the grasper (600) may pull the grasper (600) proximally relative to the distal engagement portion (708). The second segment (642) (or the tapered segment (644)) may limit the withdrawal of the grasper (600), such that the distance between the coupling magnet (718) and the grasper (600) increases. This may decrease the attractive force between the coupling magnet (718) and the grasper (600), which may allow the grasper (600) to be pulled from, released from, or otherwise fall from the distal engagement portion (708).

The coupling magnet (718) may be retracted in any suitable manner, such as described in more detail above. For example, in the variation of the delivery device (700) shown in FIGS. 7A-7D, the delivery device (700) may comprise an actuation rod (714) slidably disposed in the shaft (706). The actuation rod (714) may be configured to retract the coupling magnet (718). For example, the actuation rod (714) may be slidably disposed within a lumen (722) of the coupling magnet (718). In some variations, at least a segment of the actuation rod (714) may be sized and configured such that the portion of the actuation rod (714) cannot fully pass through the lumen (722). For example, the variation shown in FIG. 7A-7D a segment (740) of the actuation rod may have a diameter greater than a diameter of the lumen (722). Additionally or alternatively, the segment (740) may comprise one or more projections extending from an outer surface of the actuation rod (714) and which cannot fully pass through the lumen (722). When the segment (740) of the actuation rod (714) is positioned distal to the coupling magnet (718), the actuation rod (714) may be freely advanced relative to the coupling magnet (718). Conversely, withdrawal of the actuation rod (714) may pull the segment (740) of the actuation rod (714) into contact with the coupling magnet (718). Since the segment (740) cannot fully pass through the lumen (722) of the coupling magnet (718), further withdrawal of the actuation rod (714) may cause the segment of the actuation rod (714) to pull on and withdraw the coupling magnet (718). When the actuation rod (714) is subsequently advanced, the spring (720) may advance the coupling magnet (718) with the actuation rod (714) until the coupling magnet (718) reaches the advanced position.

The actuation rod (714) may be advanced or retracted relative to the shaft (706) to actuate and/or eject the grasper (600). In variations where the handle comprises a trigger (such as discussed above), the trigger may be operatively connected to the actuation rod (714), such that movement of the trigger slides the actuation rod (714). Movement of the actuation rod (714) may rotate the first jaw (602) of the grasper (600). Specifically, when the grasper (600) is coupled to the delivery device (700) (as shown in FIG. 7B), the actuation rod (714) may be aligned with the lumen (612) of the barrel portion (610) such that the actuation rod (714) enters the lumen (612). As the actuation rod (714) is advanced into the lumen (612), the actuation rod (714) may press against the proximal end (652) of the shuttle pin (650) and advance the shuttle pin (650) along the lumen (612). As the shuttle pin (650) is advanced along the lumen (612), the distal end (654) of the shuttle pin (650) may move into the channel (662) of the barrel extension (660). The distal end of the shuttle pin (650) may in turn push against the proximal arm (620) (e.g., against a portion of the proximal arm (620) that is positioned in the channel (662) and aligned with the lumen (612)). The proximal arm (620) may act as a cam to convert the linear motion of the shuttle pin (650) into rotation of the proximal arm (620), which may in turn rotate the first jaw (602) away from the second jaw (604). When the first jaw (602) is spring-biased toward the second jaw (604), the rotation of the proximal arm (620) may overcome this spring bias, which may allow the actuation rod (714) to hold the first jaw (602) in its open position, as shown in FIG. 7C.

Additionally, the first jaw (602) may rotate back toward the second jaw (604) when the actuation rod (714) is retracted. Specifically, as the actuation rod (714) is withdrawn, the return bias of the first jaw (602) may cause the proximal arm (620) to push against the shuttle pin (650), which may slide the shuttle pin (650) proximally within the lumen (612). This may return the grasper to a closed configuration, such as shown in FIG. 7B. When the grasper (600) is closed around tissue, the actuation rod (714) may be further retracted to release the grasper (600) from the delivery device (700), as discussed above. When a trigger is moveable between three positions to actuate and release the grasper (600) as discussed above, placing the trigger in the first position may position the actuation rod (714) in a position as illustrated in FIG. 7B, in which the grasper (600) may be coupled to the delivery device (700) in a closed configuration. Moving the trigger to the second position may advance the actuation rod to the position illustrated in FIG. 7C, in which the grasper (600) may be releasably coupled to the delivery device (700) in an open configuration. Moving the trigger to the third position may retract the actuation rod (714) to the position illustrated in FIG. 7D, in which the grasper (600) may be decoupled from the delivery device (700).

Additionally, in the variation of the grasper (600) shown in FIGS. 6A-6C, at least a portion of the proximal arm (620) may be exposed relative to the main body (606) (e.g., at least a portion of the proximal arm (620) may extend out of the channel (662) of the barrel extension (660)), which may allow a grasping device to grasp the proximal arm (620) to rotate the first jaw (602) relative to the second jaw (604). For example, opposing forces (represented by arrows (622) in FIG. 6C) may be applied (e.g., via a grasping device) to the exposed portion of the proximal arm (620) and the main body (606) (e.g., the barrel extension (660)) to cause the proximal arm (620) to rotate around the pivot point (608) (which may, in turn rotate the first jaw (602) away from the second jaw (604)). In these variations, the height of the walls (664) of the barrel extension (660) may limit the amount that the proximal arm (620) may be rotated (e.g., a grasping device may rotate the proximal arm (620) until the grasping device contacts the top and bottom edges of the wall). Additionally, when top and/or bottom edges of a wall of the barrel portion is curved or ramped, the curved or ramped edges may help guide a grasping device toward another section of the barrel extension (660) during grasping. Specifically, if the grasping device applies a compressive force at a ramped or curved portion of an edge, the grasping device may slide along the ramped/curved portion toward a shorter portion of the wall. For example, in the variation of the grasper (600) shown in FIGS. 6A-6C, if a grasping device applies a compressive force at either the ramped segments (682) or (684) of the top edge (666), the grasping device may slide toward the linear portion (680).

In some variations of the graspers described here, the grasper may comprise one or more coatings which may help to smooth discontinuities in the contours of the grasper and may act to provide one or more atraumatic surfaces of the grasper. The one or more coatings may comprise silicone, urethane, one or more nylon blends, polyethylenes, fluoropolymers, combinations thereof and the like. Additionally, the jaws of the graspers described above may comprise one or more features which may promote engagement with tissue. In some variations, one or more surfaces of a jaw may be roughened, which help to reduce slipping between the jaws and tissues. Additionally or alternatively, the graspers may comprise teeth or other projections which may facilitate engagement of the jaw with tissue.

In some variations, one or more jaws of the graspers described here may include a longitudinal recess extending at least partially through the jaws. For example, in the variation of the grasper (600) shown in FIGS. 6A-6C, the first jaw (602) and the second jaw (604) may each include a grasping surface (690) having a plurality of teeth (692), and may include a recess (694) extending at least partially through the grasping surface (690) and some of the teeth (692). In these variations, when the jaws are used to grasp tissue therebetween, tissue may be squeezed or captured into or otherwise enter the recess (694) of each jaw, which may help to provide a more secure hold between the grasper (600) and the tissue.

As mentioned above, the graspers described here may be used to provide remote suspension of tissue during a minimally-invasive procedure. Generally, to provide suspension of a tissue, a grasper as described herein may be advanced into the body, may be releasably connected to a tissue in the body, and may be suspended using one or more magnets positioned externally to the body to move and suspend the tissue. In some variations, the connection between the grasper and the tissue may be released, and the grasper may be repositioned and reconnected to tissue (either the same tissue or different tissue).

The grasper may be advanced into the body in any suitable manner. In some variations, the grasper may be advanced into the body through a laparoscopic port as part of a laparoscopic procedure. In some instances, the laparoscopic procedure may be a reduced port technique or single-incision laparoscopic procedure. In some variations, the grasper may be advanced into the body using a delivery device, such as the delivery device (100) described above with respect to FIGS. 1A-1C and 2A-2F. In these variations, the grasper may be releasably coupled to a distal engagement portion of the delivery device, and the distal engagement portion of the delivery device may be advanced into the body to advance and position the grasper within the body.

Once the grasper is positioned in the body, it may be releasably connected to tissue. To connect the grasper to tissue, the grasper may first be placed in an open configuration, in which a first jaw of the grasper is rotated away from a second jaw of the grasper. In some variations, the grasper may be placed in an open configuration using the delivery device carrying the grasper (e.g., by advancing an actuation rod through a barrel portion of the grasper, such as described in more detail above with respect to FIGS. 2A-2F) or by a grasping device which may engage and move the grasper to the open configuration (as described in more detail above). With the grasper in the open configuration, the grasper may be manipulated to position the tissue between the first jaw and the second jaw. The grasper may be returned to a closed configuration, in which the first jaw rotates toward the second jaw to hold the tissue between the jaws. The grasper may then be released from the delivery device and/or grasping device, and these devices may be removed from the body.

Figure 5A:
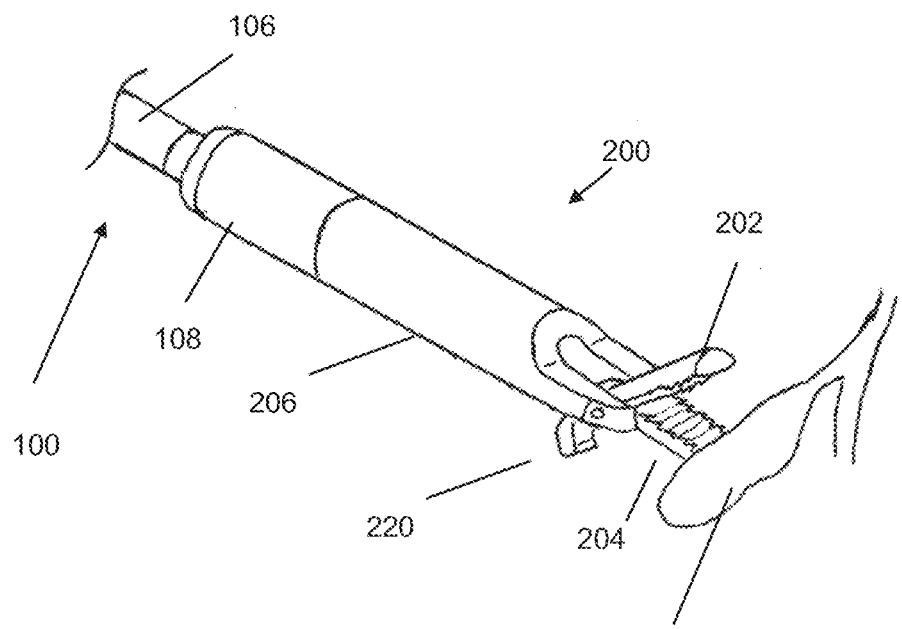
FIGS. 5A-5D depict a variation of the methods described here.
Figure 5B:
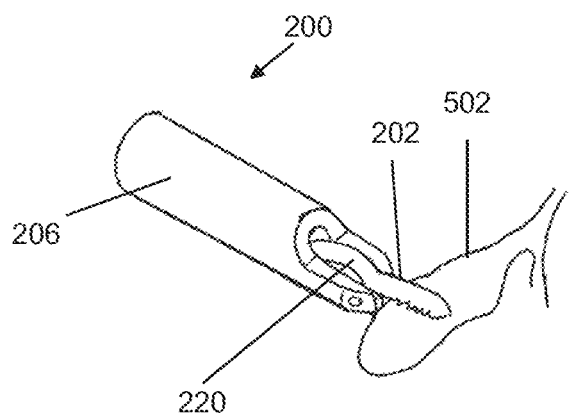

With the grasper releasably connected to the tissue, a magnetic control element comprising one or more magnets may be positioned externally of the body and may magnetically attract the grasper to reposition and/or hold the grasper. For example, FIGS. 5A-5D depict an illustrative method by which a grasper may be used to reposition and/or hold tissue. While the variations of the grasper (200) and the delivery device (100) that are described above with respect to FIGS. 1A-1C and 2A-2F are depicted in FIGS. 5A-5D, it should be appreciated that any suitable graspers and/or delivery systems as described here may perform the steps discussed below. Specifically, as shown in FIG. 5A, the grasper (200) may be advanced into the body toward a target tissue (502) (shown in FIG. 5 as a gallbladder, although it should be appreciated that the graspers described here may be releasably connected to any suitable tissue), and positioned in an open configuration. To advance the grasper (200), the grasper (200) may be releasably coupled to a distal engagement portion (108) of a delivery device (100), and a user may advance the distal engagement portion (108) into the body to position the grasper (200). The tissue (502) may be positioned between the first (202) and second (204) jaws of the grasper (200), and the grasper (200) may be moved to a closed configuration to releasably couple the grasper (200) to the tissue (502), as shown in FIG. 5B. Once connected to the tissue (502), the grasper (200) may be released from the delivery device (100), and the delivery device may be removed from the body.

Figure 5C:
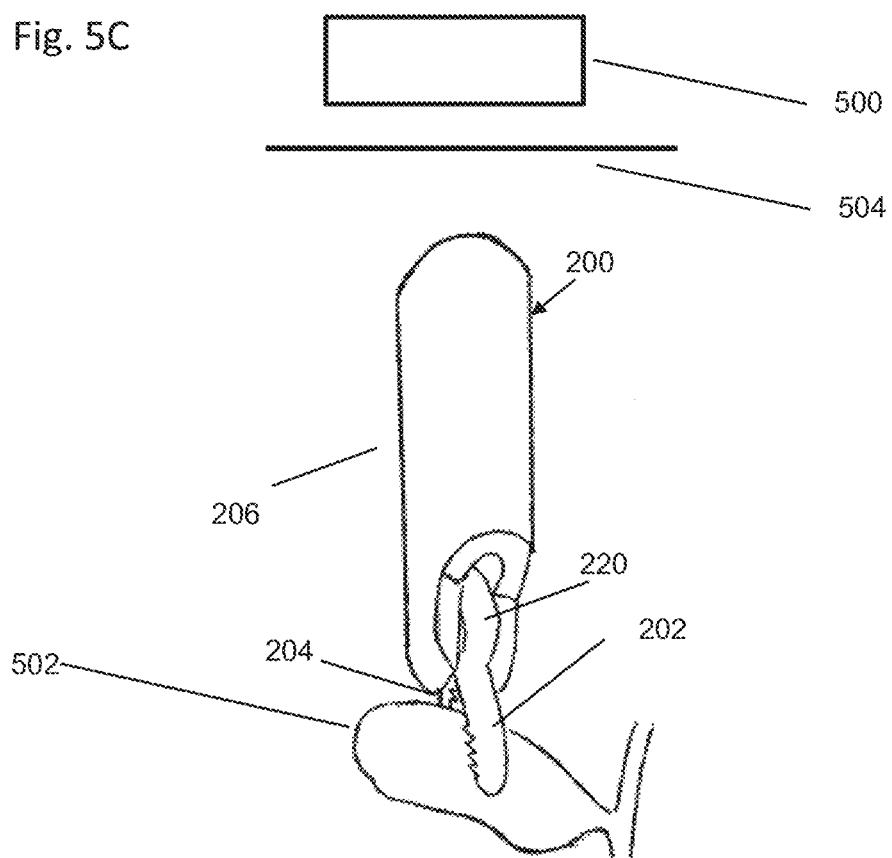

When a magnetic control device (500) is positioned externally of the body, the magnetic control device (500) may attract the grasper (200) and lift the grasper toward the magnetic control device (500). When the grasper (200) is placed in the abdomen, this may lift the grasper toward a wall (represented by line (504)) of the abdomen, such as shown in FIG. 5C. The magnetic control device may be further manipulated to reposition the grasper (200) and the tissue (502).

Figure 5D:
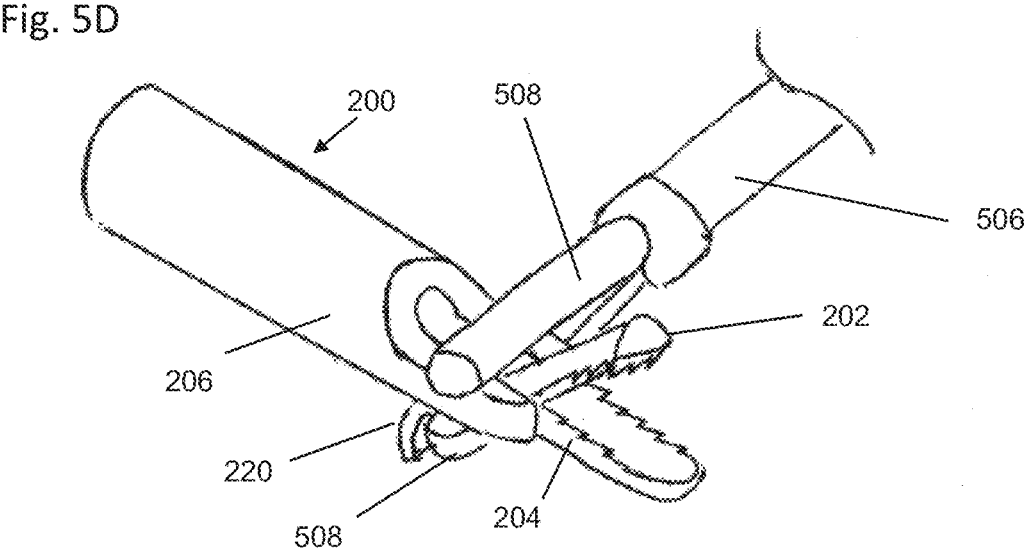

As mentioned above, in some instances it may be desirable to release the connection between the grasper (200) and the tissue (502). For example, in some instances it may be desirable to connect the grasper to a different portion of the tissue. In these instances, the grasper may be returned to an open configuration (either using one of the delivery devices described here or a grasping device, as discussed above) to release the grasper from the tissue. For example, FIG. 5D shows a grasping device (506) having opposing jaws (508) which may grab a proximal arm (220) and the main body (206) of the grasper (200) to rotate the first jaw (202) away from the second jaw (204), which may release the grasper (200) from tissue. The grasper may be repositioned to again place tissue between the jaws of the grasper, and the grasper may then be placed in the closed configuration to reconnect the grasper to tissue. In other instances, the grasper may be decoupled from the tissue, and removed from the body.

We claim:

1. A device for grasping tissue comprising:
   a main body comprising a barrel portion having a lumen extending therethrough;
   a first jaw rotatably coupled to the main body;
   a second jaw, wherein the first jaw is biased closed toward the second jaw and the first jaw is rotatably coupled to the main body about a pivot axis transverse to a longitudinal axis of the main body; and
   a proximal arm extending from the first jaw, wherein the device is configured such that a force applied to the proximal arm opens the first jaw relative to the second jaw.

2. The device of claim 1, wherein the device is configured such that removing the force applied to the proximal arm allows the first jaw to bias toward the second jaw.

3. The device of claim 1, wherein the device is configured such that advancement of an actuation rod through the lumen contacts the proximal arm and opens the first jaw relative to the second jaw.

4. The device of claim 1, wherein the device is configured such that withdrawal of an actuation rod from the lumen allows a return bias of the first jaw to close the first jaw relative to the second jaw.

5. The device of claim 1, wherein the barrel portion comprises a proximal end and a distal end, wherein a diameter of the distal end is more than a diameter of the proximal end.

6. The device of claim 1, wherein the main body comprises a tapered proximal end.

7. The device of claim 1, wherein a proximal end of the main body is rounded.

8. The device of claim 1, wherein a diameter of the barrel portion is more than a diameter of the first and second jaws in a closed configuration.

9. The device of claim 1, wherein a diameter of a proximal end of the main body is more than a diameter of a distal end of the main body.

10. The device of claim 1, wherein at least a portion of the proximal arm is exposed from the main body.

11. The system of claim 1, wherein at least a portion of the device comprises a ferromagnet.

12. The system of claim 1, wherein at least a portion of the device comprises one or more of stainless steel, iron, cobalt, nickel, neodymium iron boron, samarium cobalt, aluminum nickel cobalt alloy, ceramic ferrite, and alloys thereof.

13. The device of claim 1, wherein the first jaw is in contact with the second jaw when the first jaw is biased closed toward the second jaw.

14. A device for grasping tissue comprising:

a main body;

a first jaw rotatably coupled to the main body;

a second jaw, wherein the first jaw is rotatably coupled to the main body via a torsional spring and the first jaw is biased closed toward the second jaw; and a proximal arm extending from the first jaw, wherein the device is configured such that a force applied to the proximal arm overcomes a spring bias of the torsional spring and opens the first jaw relative to the second jaw.

15. The device of claim 14, wherein the device is configured such that removing the force applied to the proximal arm allows the first jaw to bias toward the second jaw.

16. The device of claim 14, wherein the device is configured such that advancement of an actuation rod through the lumen contacts the proximal arm and opens the first jaw relative to the second jaw.

17. The device of claim 14, wherein the device is configured such that withdrawal of an actuation rod from the lumen allows a return bias of the first jaw to close the first jaw relative to the second jaw.

18. The device of claim 14, wherein a barrel portion comprises a proximal end and a distal end, wherein a diameter of the distal end is more than a diameter of the proximal end.

19. The device of claim 14, wherein the main body comprises a tapered proximal end.

20. The device of claim 14, wherein a proximal end of the main body is rounded.

21. The device of claim 14, wherein a diameter of a barrel portion is more than a diameter of the first and second jaws in a closed configuration.

22. The device of claim 14, wherein a diameter of a proximal end of the main body is more than a diameter of a distal end of the main body.

23. The device of claim 14, wherein at least a portion of the proximal arm is exposed from the main body.

24. The device of claim 14, wherein at least a portion of the device comprises a ferromagnet.

25. The device of claim 14, wherein at least a portion of the device comprises one or more of stainless steel, iron, cobalt, nickel, neodymium iron boron, samarium cobalt, aluminum nickel cobalt alloy, ceramic ferrite, and alloys thereof.

* * * * *